United States Patent
Giralt Lledó et al.

(10) Patent No.: US 10,611,727 B2
(45) Date of Patent: Apr. 7, 2020

(54) 1-[1-(BENZOYL)-PYRROLIDINE-2-CARBONYL]-PYRROLIDINE-2-CARBONITRILE DERIVATIVES

(71) Applicants: UNIVERSITAT DE BARCELONA, Barcelona (ES); FUNDACIÓ INSTITUT DE RECERCA BIOMÈDICA (IRB BARCELONA), Barcelona (ES); IPROTEOS S.L., Barcelona (ES)

(72) Inventors: Ernest Giralt Lledó, Barcelona (ES); Teresa Tarragó Clua, Barcelona (ES); Roger Prades Cosano, Barcelona (ES); Soledad Royo Gracia, Barcelona (ES)

(73) Assignees: UNIVERSITAT DE BARCELONA, Barcelona (ES); FUNACIÓ INSTITUT DE RECERCA BIOMÉDICA, Barcelona (ES); IPROTEOS S.L., Barcelona (ES)

( * ) Notice: Subject to any disclaimer, the term of this patent is extended or adjusted under 35 U.S.C. 154(b) by 0 days.

(21) Appl. No.: 16/142,907

(22) Filed: Sep. 26, 2018

(65) Prior Publication Data
US 2019/0084927 A1 Mar. 21, 2019

Related U.S. Application Data

(62) Division of application No. 14/436,715, filed as application No. PCT/EP2013/073460 on Nov. 11, 2013, now Pat. No. 10,125,097.

(30) Foreign Application Priority Data

Nov. 12, 2012 (EP) .................................... 12382446

(51) Int. Cl.
*C07D 207/16* (2006.01)
*C07D 403/06* (2006.01)

(52) U.S. Cl.
CPC ......... *C07D 207/16* (2013.01); *C07D 403/06* (2013.01)

(58) Field of Classification Search
CPC .............................. C07D 207/16; C07D 403/06
See application file for complete search history.

(56) References Cited

U.S. PATENT DOCUMENTS

| | | | |
|---|---|---|---|
| 6,159,938 A | 12/2000 | Gyorkos et al. | |
| 7,173,024 B2 | 2/2007 | Gynther et al. | |
| 10,125,097 B2 | 11/2018 | Lledó et al. | |
| 2006/0100253 A1 | 5/2006 | Niestroj et al. | |
| 2006/0229254 A1 | 10/2006 | Gynther et al. | |
| 2008/0269313 A1 | 10/2008 | Sirvio et al. | |
| 2010/0081701 A1 | 4/2010 | Evans | |

FOREIGN PATENT DOCUMENTS

| | | |
|---|---|---|
| DE | 19603510 A1 | 8/1997 |
| JP | 2011037874 A | 2/2011 |
| WO | WO 03/004468 A1 | 1/2003 |
| WO | WO 2004/060862 A2 | 7/2004 |
| WO | WO 2005/002624 A1 | 1/2005 |
| WO | WO 2005/027934 A1 | 3/2005 |
| WO | WO 2008/077978 A1 | 7/2008 |
| WO | WO 2010/083570 A1 | 7/2010 |

OTHER PUBLICATIONS

Lopez et al. Expert Opinion on Therapeutic Patents, 2011, vol. 21, No. 7, pp. 1023-1044 (Year: 2011).*
Wilk, S., et al., "Minireview Prolyl Endopeptidase," *Life Sci.* 33:2149-2157, Pergamon Press Ltd., United Kingdom (1983).
Yoshimoto, T., et al., "Specific Inhibitors for Prolyl Endopeptidase and Their Anti-Amnesic Effect," *J. Pharmacobiodyn.* 10:730-735, Elsevier, Netherlands (1987).
Kowall, N. W., et al., "An In Vivo Model for the Neurodegeneratice Effects of Beta Amyloid and Protection by Substance P," *Proc. Natl. Acad. Sci. USA* 88(16):7247-7251, United States National Academy of Sciences, United States (1991).
O'Leary, R.M. and O'Connor, B., "Thyrotropin-Releasing Hormone," *J. Neurochem.* 65:953-963, Wiley-Blackwell, United States (1995).
Komatsu, Y., "GABA Receptors, Monoamine Receptors, and Postsynaptic Inositol Trisphosphate-Induced CA2+ Release Are Involved in the Induction of Long-Term Protentiation at Visual Cortical Inhibitory Synapses," *J. Neurosci.* 16:6342-6352, Society for Neuroscience, United States (1996).
Mantle, D., et al., "Comparison of Proline Endopeptidase Activity in Brain Tissue From Normal Cases and Cases With Alzheimer's Disease, Lewy Body Dementia, Parkinson's Disease and Huntington's Disease," *Clin. Chim. Acta* 249(1-2):129-139, Elsevier, Netherlands (1996).
Shinoda, M., et al., "Pharmacological Studies of a Novel Prolyl Endopeptidase Inhibitor, JTP-4819, in Rats With Middle Cerebral Artery Occlusion," *Eur. J. Pharmacol.* 305(1-3):31-38, Elsevier, Netherlands (1996).

(Continued)

*Primary Examiner* — James D. Anderson
(74) *Attorney, Agent, or Firm* — Sterne, Kessler, Goldstein & Fox P.L.L.C.

(57) ABSTRACT

The present invention relates to 1-[1-(benzoyl)-pyrrolidine-2-carbonyl]-pyrrolidine-2-carbonitrile derivatives having pharmacological activity formula (I) to processes of preparation of such compounds, to pharmaceutical compositions comprising them, and to their use in therapy and/or prophylaxis of a cognitive disorder.

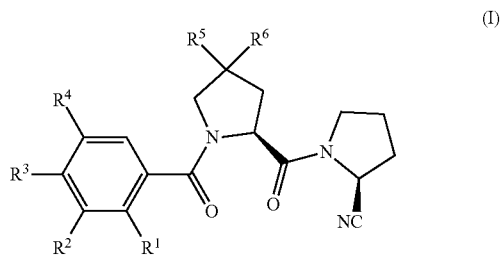

(I)

19 Claims, 1 Drawing Sheet

(56) References Cited

OTHER PUBLICATIONS

Kato, A., et al., "Prevention of Amyloid-Like Deposition by a Selective Prolyl Endopeptidase Inhibitor, Y-29794, in Senescence-Accelerated Mouse," *J. Pharmacol. Exp. Ther.* 283(1):328-335, American Society for Pharmacology and Experimental Therapeutics, United States (1997).

Polymeropoulos, M. H., et al., "Mutation in the Alpha-Synuclein Gene Identified in Families With Parkinson's Disease," *Science* 276(5321):2045-2047, American Association for the Advancement of Science, United States (1997).

Toide, K., et al., "Effect of a Novel Prolyl Endopeptidase Inhibitor, JTP-4819, on Spatial Memory and Central Cholinergic Neurons in Aged Rats," *Pharmacol. Biochem. Behav.* 56(3):427-434, Elsevier, Netherlands (1997).

Toide, K., et al., "A Novel Prolyl Endopeptidase Inhibitor, JTP-4819 Its Behavioral and Neurochemical Properties for the Treatment of Alzheimer's Disease," *Rev. Neurosci.* 9(1):17-29, Nature Publishing Group, United Kingdom (1998).

Katsube, N., et al., "ONO-1603, A Potential Antidementia Drug, Delays Age-Induced Apoptosis and Suppresses Overexpression of Glyceraldehyde-3-Phosphate Dehydrogenase in Cultured Central Nervous System Neurons," *J. Pharmacol. Exp. Ther.* 288(1):6-13, American Society for Pharmacology and Experimental Therapeutics, United States (1999).

Williams, RS et al., "Loss of a Prolyl Oligopeptidase Confers Resistance to Lithium by Elecation of Inositol (1,4,5) Trisphosphate," *Embo J.* 18:2734-2745, Nature Publishing Group, United Kingdom (1999).

Hsu, L. J., et al., "Alpha-Synuclein Promotes Mitochondrial Deficit and Oxidative Stress," *Am. J. Pathol.* 157(2):401-410, Elsevier, Netherlands (2000).

Marighetto, A., et al., "Further Evidence for a Dissociation Between Different Forms of Mnemonic Expressions in a Mouse Model of Age-Related Cognitive Decline: Effects of Tacrine and S 17092, a Novel Prolyl Endopeptidase Inhibitor," *Learn. Mem.* 7(3):159169, Cold Spring Harbor Laboratory Press, United States (2000).

Masliah, E., et al., "Dopaminergic Loss and Inclusion Body Formation in Alpha-Synuclein Mice: Implications for Neurodegenerative Disorders," *Science* 287(5456):1265-1269, American Association for the Advancement of Science, United States (2000).

Morain, P., et al., "Pharmacodynamic and Pharmacokinetic Profile of 2 17092, a New Orally Active Proll Endopeptidase Inninitor, in Elderly Healthy Volunteers. A Phase I Study," *Br. J. Clin. Pharmacol.* 50(4):350-9, Wiley-Blackwell, Hoboken, United States (2000).

Gosavi, N., et al., "Golgi Fragmentation Occurs in the Cells With Prefibrillar Alpha-Synuclein Aggregates and Precedes the Formation of Fibrillar Inculsion," *J. Biol. Chem.* 277(50):48984-48992, American Society for Biochemistry and Molecular Biology, United States (2002).

Morain, P., et al., "S 17092: A Prolyl Endopeptidase Inhibitor as a Potential Therapeutic Drug for Memory Impairment. Prelinical and Clinical Studies," *CNS Drug. Rev.* 8(1):31-52, American Society for Biochemistry and Molecular Biology, United States (2002).

Schneider, J. S., et al., "Effects of Prolyl Endopeptidase Inhibitor S 17092 on Cognative Deficitys in Chronic Low Dose MPTP-Treated Monkeys," *Neuropsychopharmacology* 26(2):176-182, Nature Publishing Group, United Kingdom (2002).

Schulz, I., et al., "Modulation of Inositol 1,4,5-Triphosphate Concentration by Prolyl Endopeptidase Inhibition," *Eur. J. Biochem.* 269:5813-5820, John Wiley & Sons, United States (2002).

Yang, F., et al., "AC-SDKP Reverses Inflammation and Fibrosis in Rats With Heart Failure After Myocardial Infarction," *Hypertension* 43(2):229-236, American Heart Association, United States (2004).

Zarranz, J. J., et al., "The New Mutation, E46K, of Alpha-Synuclein Causes Parkinson and Lewy Body Dementia," *Ann. Neurol.* 55(2):164-173, John Wiley & Sons, United States (2004).

Bennett, M. C., "The Role of Alpha-Synuclein in Neurodegeneratice Diseases," *Pharmacol. Ther.* 105(3):311-331, Elsevier, Netherlands (2005).

Cheng, L., et al., "How Can the Mood Stabilizer VPA Limit Both Mania and Depression?" *Mol. Cell. Neurosci.* 29:155-161, Elsevier, Netherlands (2005).

Rossner, S., et al., "Brain Prolyl Endopeptidase Expression in Aging, APP Transgenic Mice and Alzheimer's Disease," *Neurochem. Res.* 30(6-7):695-702, Springer Science+Business Media, Germany (2005).

Morain, P., et al., "Psychotropic Profile of S 17092, a Prolyl Endopeptidase Inhibitor, Using Quantitative EEG in Young Healthy Volunteers," *Neuropsychobiology* 55(3-4):176-183, Karger Publishers, Switzerland (2007).

Brandt, I., et al., "Prolyl Oligopeptidase Stimulates the Aggregation of Alpha-Synuclein," *Peptides* 29(9):1472-1478, Elsevier, Netherlands (2008).

Klegeris, A., et al., "Prolyl Endopeptidase Is Revealed Following Silac Analysis to Be a Novel Mediator of Human Microglial and THP-1 Cell Neurotoxicity," *Glia* 56(6):675-685, John Wiley & Sons, United States (2008).

Hirsch, E. C., et al., "Neuroinflammation in Parkinson's Disease: A Target for Neuroprotection?" *Lancet Neurol.* 8(4):382-397, Elsevier, Netherlands (2009).

Nolte, W. M., et al., "Peptidomics of Prolyl Endopeptidase in the Central Nervous System," *Biochemistry* 48(50):11971-11981, American Chemical Society, United States (2009).

Park, D. H., et al., "Subchronic Administration of Rosmarinic Acid, a Natural Prolyl Oligopeptidase Inhibitor, Enhances Cognitive Performances," *Fitoterapia* 81(6):644-648, Elsevier, Netherlands (2010).

Tenorio-Laranga, J., et al., "Prolyl Oligopeptidase Is Inhibited in Relapsing-Remitting Multiple Sclerosis," *J Neuroinflammation* 7:23, BioMed Central, United Kingdom (2010).

Philips, T., et al., Neuroinflammation in Amyotropic Lateral Sclerosis: Role of Glial Activation in Motor Neuron Disease, *Lancet Neurol.* 10(3):253-263, Elsevier, Netherlands (2011).

Myohanen, T. T., et al., "A Prolyl Oligopeptidase Inhinitor, KYP-2047, Reduces Alpha-Synuclein Protein Levels and Aggregates in Cellular and Animal Models of Parkinson's Disease," *Br. J. Pharmacol.* 166(3):1097-1113, Wiley-Blackwell, United States (Jun. 2012).

Bardgett, M. E., et al., "NMDA receptor blockade and hippocampal neuronal loss impair fear conditioning and position habit reversal in C57B1/6 mice," *Brain Research Bulletin* 60(1-2):131-142, Elsevier Science Inc., Unites States (2003).

Boess, F. G., et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," *J. Pharmacol. Exp. Ther.* 321(2) :716-725, The American Society for Pharmacology and Experimental Therapeutics, Unites States (2007).

Boess, F. G., et al., "Inhibition of phosphodiesterase 2 increases neuronal cGMP, synaptic plasticity and memory performance," *Neuropharmacology* 47(7):1081-1092, Elsevier Ltd., United Kingdom (2004).

Castellano, C., et al., "NMDA Receptors and Learning and Memory Processes", *Current Drug Targets* 2(3):273-283, Bentham Science Publishers, United Arab Emirates (2001).

Dere, E., et al., "The pharmacology, neuroanatomy and neurogenetics of one-trial object recognition in rodents," *Neuroscience & Biobehavioral Reviews* 31(5):673-704, Elsevier Ltd., United Kingdom (2007).

D'Hooge, R., et al., "Applications of the Morris water maze in the study of learning and memory," *Brain Research Reviews* 36(1):60-90, Elsevier Science B.V., Netherlands (2001).

Di, L., et al., "High throughput artificial membrane permeability assay for blood-brain barrier," *European Journal of Medicinal Chemistry* 38(3):223-232, Éditions scientifiques et médicales Elsevier SAS, Netherlands (2003).

Ennaceur, A., et al., "A new one-trial test for neurobiological studies of memory in rats. 1: Behavioral data," *Behavioural Brain Research* 31(1):47-59, Elsevier Science Publishers B.V., Netherlands (1988).

(56) References Cited

OTHER PUBLICATIONS

Kansy, M., et al., "Physicochemical High Throughput Screening: Parallel Artificial Membrane Permeation Assay in the Description of Passive Absorption Processes," *J. Med. Chem.* 41(7):1007-1010, American Chemical Society, United States (1998).

Madder, A., et al., "A Novel Sensitive Colorimetric Assay for Visual Detection of Solid-Phase Bound Amines.," *Eur. J. Org. Chem.* 1999(11):2787-2791, Wiley-VCH, Germany (1999).

Mutlu, O., et al., "Effects of olanzapine, sertindole and clozapine on MK-801 induced visual memory deficits in mice," *Pharmacology, Biochemistry and Behavior* 99(4):557-565, Elsevier Inc., United States (2011).

Riedel, G., et al. "Glutamate receptor function in learning and memory," *Behavioural Brain Research* 140:1-47, Elsevier Science B.V., Netherlands (2003).

Sarter, M., et al., "Behavioral screening for cognition enhancers: from indiscriminate to valid testing: Part I," *Psychopharmacology* 107:144-159, Springer Verlag, Germany (1992).

Spowart-Manning, L., et al., "The T-maze continuous alternation task for assessing the effects of putative cognition enhancers in the mouse," *Behavioural Brain Research* 151:37-46, Elsevier B.V., Netherlands (2004).

Tarragó, T., et al., "Identification by $^{19}$F NMR of Traditional Chinese Medicinal Plants Possessing Prolyl Oligopeptidase Inhibitory Activity," *ChemBioChem* 7(5):827-833, Wiley-VCH, Germany (2006).

Toide, K., et al., "JTP-4819: a novel prolyl endopeptidase inhibitor with potential as a cognitive enhancer," *J. Pharmacol. Exp. Ther.* 274(3):1370-1378, The American Society for Pharmacology and Experimental Therapeutics, United States (1995).

van der Staay, F. J., et al., "Effects of the cognition impairer MK-801 on learning and memory in mice and rats," *Behavioural Brain Research* 220(1):215-229, Elsevier B.V., Netherlands (2011).

English language abstract for DE 19603510 A1 (FP1), Espacenet, European Patent Office, accessed Dec. 11, 2018.

International Search Report for International Application No. PCT/EP2013/073460, European Patent Office, Netherlands, dated Dec. 12, 2013, 3 pages.

International Preliminary Report on Patentability for International Application No. PCT/EP2013/073460, The International Bureau of WIPO, Geneva, Switzerland, dated May 12, 2015, 7 pages.

Extended European Search Report for European Application No. EP 12382446, European Patent Office, The Hague, Netherlands, dated Mar. 12, 2013, 5 pages.

Office Action dated May 5, 2017, in U.S. Appl. No. 14/436,715, having a 371(c) date of Apr. 17, 2015, 8 pages.

Office Action dated Nov. 6, 2017, in U.S. Appl. No. 14/436,715, having a 371(c) date of Apr. 17, 2015, 10 pages.

Notice of Allowance dated Jun. 21, 2018, in U.S. Appl. No. 14/436,715, having a 371(c) date of Apr. 17, 2015, 9 pages.

\* cited by examiner

1-[1-(BENZOYL)-PYRROLIDINE-2-CARBONYL]-PYRROLIDINE-2-CARBONITRILE DERIVATIVES

FIELD OF THE INVENTION

The present invention relates to compounds having pharmacological activity, and more particularly to some 1-[1-(benzoyl)-pyrrolidine-2-carbonyl]-pyrrolidine-2-carbonitrile derivatives, to processes of preparation of such compounds, to pharmaceutical compositions comprising them, and to their use in therapy and/or prophylaxis of cognitive disorders.

BACKGROUND

Prolyl oligopeptidase (EC 3.4.21.26) (POP), also known as prolyl endopeptidase (PREP), is a serine protease that catalyses the hydrolysis of peptides at the C-terminal side of L-proline residues. It is widely distributed in mammals and can be purified from various organs, including the brain.

The enzyme plays an important role in the breakdown of proline-containing neuropeptides related to learning and memory functions (Wilk S et al., *Life Sci.* 1983; 33:2149-57; O'Leary R M, O'Connor B. *J. Neurochem.* 1995; 65:953-63).

The effects of prolyl oligopeptidase inhibition have been tested in the treatment of cognitive deficits related to neurodegenerative processes. Parkinson's disease was generated in monkeys by treatment with 1-methyl-4-phenyl-1,2,3,6-tetrahydropyridine (MPTP), a neurotoxin that produces depletion of substance P. Subsequent treatment with S-17092, a potent POP inhibitor, increased the performance of cognitive tasks (Schneider J S et al., *Neuropsychopharmacology* 2002; 26(2):176-82). It has also been found that POP inhibition prevents the oligomerization of α-synuclein ex vivo [Myöhänen T T et al., *Br. J. Pharmacol.* 2012; 166(3):1097-113]. In the case of Alzheimer's disease (AD), several in vivo experiments in animal models showed that POP inhibition led to neuroprotective and cognition-enhancing effects (Kato A et al., *J. Pharmacol. Exp. Ther.* 1997; 283(1):328-35 and Toide K et al., *Rev. Neurosci.* 1998; 9(1):17-29). Neuroprotective effects were originally observed by Katsube's group, when cortical and cerebellar granule cells were prevented from age-induced apoptosis by treatment with the POP inhibitor ONO-1603 (Katsube N et al., *J. Pharmacol. Exp. Ther.* 1999:288(1):6-13).

Clinical trials with POP inhibitors in the treatment of cognitive deficits have been performed only in a few cases. In a phase I clinical study Morain's group (Morain P et al., *Br. J. Clin. Pharmacol.* 2000; 50(4):350-9) found that S 17092, a new orally active prolyl endopeptidase inhibitor, showed cognition-enhancing properties in healthy elderly subjects and a clear dose-dependency; moreover, no adverse effects were detected. Later studies suggested additional slight mood-stabilizing properties for this compound (Morain P et al., *Neuropsychobiology* 2007; 55(3-4):176-83).

Prolyl oligopeptidase activity has been reported to be altered (post-mortem) in several neurodegenerative diseases, including Alzheimer's disease (AD), Parkinson's disease, Huntington's disease and multiple sclerosis (MS) (Mantle D et al., *Clin. Chim. Acta* 1996; 249(1-2):129-39).

There is also a substantial amount of evidence pointing to a role for neuroinflammation in the pathogenesis of neurodegenerative diseases such as AD, MS and Parkinson's disease (Hirsch E C et al., *Lancet Neurol.* 2009; 8(4):382-97, Philips T et al., *Lancet Neurol.* 2011; 10(3):253-63). POP has been considered to be the main enzyme implicated in the release of an anti-inflammatory tetrapeptide Ac-SDKP from Tβ4 in the brain (Yang F et al., *Hypertension* 2004; 43(2): 229-36, Nolte W M et al., *Biochemistry* 2009; 48(50):11971-81). This suggests that the inhibition of POP may help reduce neuroinflammation and consequently POP inhibitors may be useful in the treatment of neurodegenerative diseases with an inflammatory component such as Alzheimer's and Parkinson's disease and in particular help improve the cognitive disorders associated with these diseases.

Senile plaques spreading over the cortical brain areas are typical neuropathological hallmarks of AD. The main protein component of these plaques is amyloid β-peptide (Aβ). Deposition of Aβ triggers neuronal dysfunction and death in the brain. This peptide derives from the β-amyloid precursor protein (APP). Under normal conditions, APP is cleaved by α-secretase to generate soluble APPα which precludes Aβ generation.

Interestingly, POP inhibition increases intracellular IP3 levels, which may contribute to the stimulation of APPα production, which would in turn decrease Aβ generation.

Additionally, Rossner (Rossner S et al., *Neurochem. Res.* 2005; 30(6-7):695-702) found less POP immunoreactive neurons in brain structures of AD patients affected by Aβ plaques.

Additionally it seems that substance P can suppress neurotoxic action of β-amyloid protein (Kowall N W et al., *Proc. Natl. Acad. Sci. USA* 1991; 88(16):7247-51). Prolyl oligopeptidase inhibitors inhibit the metabolism of substance P helping to sustain levels of substance P that may suppress the neurotoxic action of β-amyloid protein.

In view of the above mentioned effects, it is thought that prolyl oligopeptidase inhibitors may be useful drugs for the treatment of Alzheimer's disease helping to improve the cognitive disorders associated with the disease.

Prolyl oligopeptidase has also been associated with several factors that might be relevant to multiple sclerosis (MS). For instance, POP is involved in the regulation of microglia toxicity (Klegeris A et al., *Glia* 2008; 56(6):675-85). Indeed, a recent report established a direct connection between POP and MS; the plasma POP activities of patients with RR-MS were significantly reduced (Tenorio-Laranga J et al., *J Neuroinflammation* 2010; 7:23). Interestingly, the reduction correlated with the severity of disease symptoms, but not with patient age. Instead, an inverse correlation between POP activity and age was observed in healthy controls, and in elderly controls the levels were comparable to those found in MS patients.

The neuropathological hallmark of Parkinson's disease is the progressive degeneration of melanised dopaminergic neurons in substantia nigra pars compacta together with intracellular inclusions known as Lewy bodies. A major component of the Lewy bodies is a 140 amino acid protein, α-synuclein. Under certain conditions, α-synuclein monomers interact to form prefibriliar aggregates or protofibrils, which can create cytotoxic insoluble fibrils. These fibrils cannot be degraded by the proteasome, and they impair the function of this intracellular proteolytic system. This leads to an accumulation of α-synuclein protofibrils (and other proteins that are degraded by the proteasome) in the cytosol (Bennett M C, *Pharmacol. Ther.* 2005; 105(3):311-31) and as a consequence, α-synuclein protofibrils are increased in brains of Parkinson's disease patients. These fibrils have been associated with neurotoxicity in α-synuclein overexpressing cells and mouse models (Masliah E et al., *Science* 2000; 287(5456): 1265-9; Gosavi N et al., *J. Biol. Chem.* 2002; 277(50):48984-92). Abnormal accumulation of misfolded α-synuclein may lead to mitochondrial changes which can promote oxidative stress and evoke cell death (Hsu L J et al., *Am. J. Pathol.* 2000; 157(2):401-10). Furthermore, three point mutations (A53T, A30P or E48K) in the α-synuclein gene are known to be involved in the pathogenesis of familial form of Parkinson's disease (Polymeropoulos M H et al., *Science* 1997; 276(5321):2045-7; Zarranz J J et al., *Ann. Neurol.* 2004; 55(2):164-73).

It has been shown in vitro that the aggregation rate of α-synuclein was enhanced when the protein was incubated with a clone of wild-type porcine POP, and this enhancement depended upon the POP concentration (Brandt I et al., *Peptides* 2008; 29(9):1472-8). Moreover, a mutated variant without POP activity (S544A) did not accelerate the aggregation rate.

Enhanced aggregation could also be prevented by the addition of POP inhibitors, suggesting that the effect was dependent on the POP enzymatic activity. Recent evidence has suggested that POP inhibitors can block the increased α-synuclein aggregation induced by oxidative stress in human α-synuclein overexpressing neuroblastoma SH-SY5Y cells Myöhänen T T et al., *Br J. Pharmacol* 2012; 166(3):1097-113. POP colocalizes with α-synuclein in SH-SY5Y cells, and this colocalization disappears after incubation with POP inhibitors, pointing to an interaction between POP and α-synuclein. A 5-day treatment with a POP inhibitor reduced the amount of soluble α-synuclein in the brains of a A30P α-synuclein transgenic mice.

Thus, inhibition of brain POP activity could prevent α-synuclein aggregation and thus, prevent the formation of the cytotoxic protofibrils present in the Lewy bodies. Therefore, POP inhibitors could potentially have therapeutical value in the treatment of neurodegenerative disorders where accelerated α-synuclein aggregation has been described.

Compounds capable of inhibiting POP are effective for preventing experimental amnesia induced by scopolamine in rats, inferring that POP inhibitors have functions in the alleviation of mnemonic dysfunctions (Yoshimoto T et al., *J. Pharmacobiodyn.* 1987; 10:730-5).

The effect of subchronic administration of rosmarinic acid, a non-competitive POP inhibitor (with a relatively high IC50 value of 63.7 μM), was tested in the Morris water maze in rats, and an enhancement in spatial memory was reported (Park D H et al., *Fitoterapia* 2910; 81(6):644-8).

It has been found that patients with bipolar disorder have high levels of activity of the POP in serum. In recent years, POP has gained importance as a target for the treatment of this disease, especially due to his involvement in the metabolism of inositol-1,4,5-P3 (IP3). IP3 is a key molecule in the transduction of the signal in the cascade of neuropeptides. Through the binding to specific receptors, neuropeptides induce an increase of IP3, which binds to its receptor on the membrane of the endoplasmic reticulum and induces the release of Ca2+, which is believed to play a crucial role in learning and memory. Recent findings have shown that the POP modulates the concentration of IP3 (Komatsu Y *J. Neurosci.* 1996; 16:6342-52). Thus it is known that a disruption of the gene of the POP in the eukaryotic *Dictyostelium discoideum* induces resistance to lithium via elevation of IP3 (Schulz I et al., *Eur. J. Biochem.* 2002; 289:5813-20), and also reduced the proteolytic activity of POP, which is responsible for the high concentration IP3 in glioma cells antisense human for POP. This effect is also observed when these cells are treated with specific POP inhibitors (Williams R S et al., *EMBO J.* 1999; 18:2734-45).

The IP3 signaling pathway is involved in the action of several drugs therapeutic mood stabilizers (lithium, carbamazepine and valproic acid) and defects in the mechanisms that regulate the IP3 signaling may cause bipolar disorder. Moreover, the mood stabilizer drug that is commonly used to treat bipolar disorder, valproic acid, directly inhibits the activity of recombinant POP (Cheng L et al., *Mol. Cell. Neurosci.* 2005; 29:155-61). In summary, there is strong evidence that POP inhibitors are useful in the prevention and/or treatment of bipolar affective disorder in mammals. Thus, to provide novel inhibitors of POP is interesting in the therapy of this disorder or disease.

In summary, the effects of several POP inhibitors in various cognitive tasks have been characterized, and there is some kind of consensus that POP inhibitors have positive effects on learning and memory (Morain P et al., *CNS Drug. Rev.* 2002; 8(1):31-52; Shinoda M et al., *Eur. J. Pharmacol.* 1996; 305(1-3):31-8; Marighetto A et al., *Learn. Mem.* 2000; 7(3):159-69; Toide K et al., *Pharmacol. Biochem. Behav.* 1997; 56(3):427-34; Schneider J S et al., *Neuropsychopharmacology* 2002; 26(2):176-82).

Several patents and patent applications disclose POP inhibitors: WO 2008/077978 A1, WO 2005/027934 A1, JP 2011-037874 A2, WO 2005/002624 A1, WO 2004/060862 A2, WO 03/04468 A1; DE 196 03 510 A1, US 2006/0100253 A1 and U.S. Pat. No. 6,159,938 A, but only a few compounds have undergone in vivo studies (JTP-4819, S 17092, Z-321, ONO-1603, Y-29794, ZTTA, Z-Pro-Prolinal, and KYP-2047), only the first three in the list have entered clinical trials and none of them has reached the market place.

In spite of the existence of POP inhibitors, there is still a need in the art to provide alternative compounds with a high affinity to POP and a good capacity to cross the blood-brain barrier to reach the brain where the action of the inhibitor takes place when used to treat cognitive disorders. This is an important feature for the compounds to be good candidates for use in the therapy of cognitive disorders.

BRIEF DESCRIPTION OF THE INVENTION

The inventors have now successfully found that a series of 1-[1-(benzoyl)-pyrrolidine-2-carbonyl]-pyrrolidine-2-carbonitrile derivatives are not only capable of inhibiting POP with a high potency but are also capable of crossing a parallel artificial membrane which is a well accepted method for predicting the capacity to cross the blood-brain barrier. These two properties make the compounds of the present invention ideal candidates for use in the therapy of cognitive disorders.

Therefore, one aspect of the invention relates to compounds having the formula (I):

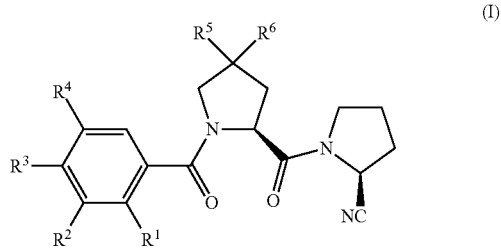

wherein
$R^1$, $R^2$, $R^3$ and $R^4$ are independently selected from the group consisting of $C_{1-4}$alkoxy, $C_{1-4}$alkylcarbonyloxy, benzyloxy, phenylcarbonyloxy, naphthylcarbonyloxy, quinolinylcarbonyloxy, isoquinolinylcarbonyloxy, trifluoromethyl, halogen and hydrogen;

$R^5$ is selected from the group consisting of halogen, nitrile, $C_{1-4}$alkoxy, $C_{1-4}$alkylthio, $C_{1-4}$alkyl, $C_{1-4}$alkylcarbonyloxy, phenyl phenoxy, phenylthio and trifluoromethyl;

$R^6$ is selected from the group consisting of hydrogen, fluor and methyl;

or a pharmaceutically acceptable salt, isomer, prodrug or solvate thereof.

Another aspect of this invention refers to processes for the preparation of a compound of formula (I) as defined above or a pharmaceutically acceptable salt, isomer, prodrug or solvate thereof.

Another aspect of this invention refers to a medicament or pharmaceutical composition comprising at least one compound of formula (I) as defined above, or a pharmaceutically acceptable salt, isomer, prodrug or solvate thereof and a pharmaceutically acceptable carrier, adjuvant or vehicle.

Another aspect of this invention refers to a compound of formula (I) as defined above, or a pharmaceutically acceptable salt, isomer, prodrug or solvate thereof, for use as a medicament, particularly for the prevention and/or treatment of cognitive disorders.

Another aspect of this invention refers to a method for the treatment or prophylaxis of cognitive disorders in a mammal wherein a therapeutic amount of a compound of formula (I) as defined above, or a pharmaceutically acceptable salt, isomer, prodrug or solvate thereof, is administered to a patient in need of said treatment. In a particular embodiment the disorder is a cognitive disorder associated with a disease selected from the group consisting of schizophrenia, bipolar affective disorder, Alzheimer's disease and Parkinson's disease.

Another aspect of this invention refers to the use of a compound of formula (I) as defined above, or a pharmaceutically acceptable salt, isomer, prodrug or solvate thereof, for the preparation of a medicament, particularly for the prevention and/or treatment of cognitive disorders and more particularly a cognitive disorder associated with a disease selected from the group consisting of schizophrenia, bipolar affective disorder, Alzheimer's disease and Parkinson's disease. These aspects and preferred embodiments thereof are additionally also defined in the claims.

DETAILED DESCRIPTION OF THE INVENTION

Figure 1:
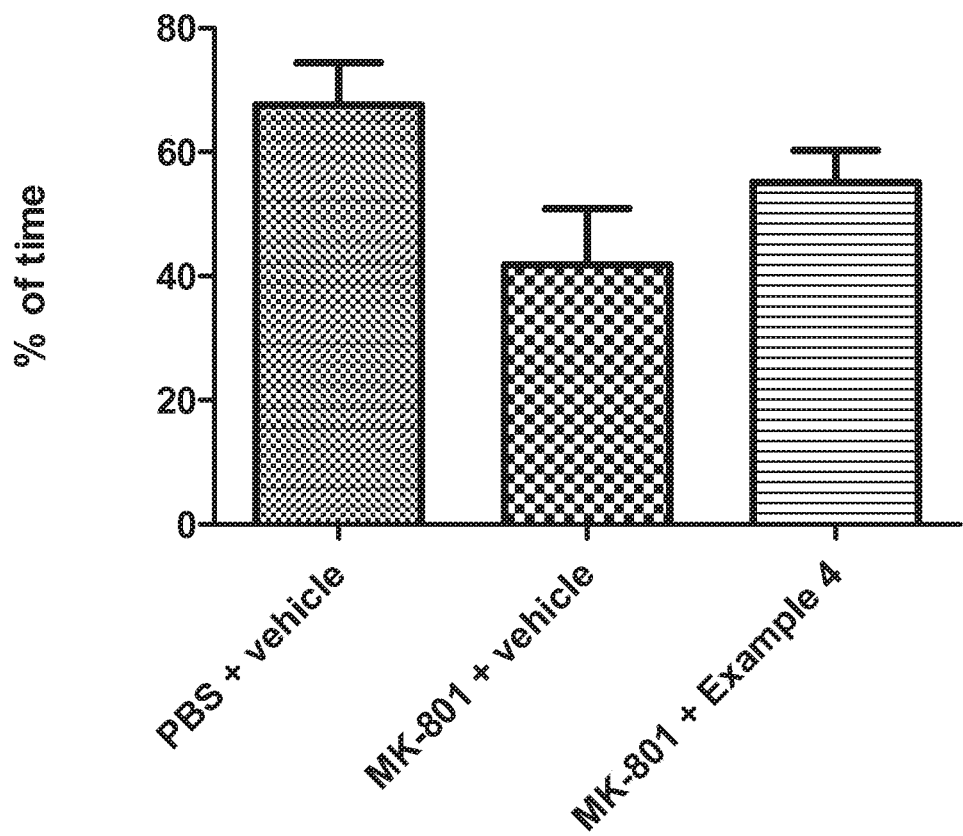
FIG. 1 is graphic comparing the results obtained in the novel object recognition (NOR) test for PBS+vehicle, MK-801+vehicle and MK-801 and the compound of example 4

In the context of the present invention, the following terms have the meaning detailed below.

As used herein $C_{1-4}$alkyl, as a group or part of a group, defines straight or branched chain saturated hydrocarbon radicals having from 1 to 4 carbon atoms such as methyl, ethyl, n-propyl, i-propyl, n-butyl, i-butyl, sec-butyl and tert-butyl. Alkyl radicals may be optionally substituted by one or more substituents such as an aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

The term $C_{1-4}$alkoxy means $C_{1-4}$alkyloxy or a $C_{1-4}$alkoxy ether radical, wherein the term $C_{1-4}$alkoxy is as defined above. Examples of suitable alkyl ether radicals include methoxy, ethoxy, n-propoxy, iso-propoxy, n-butoxy, i-butoxy, sec-butoxy and tert-butoxy.

The term $C_{1-4}$ alkylcarbonyloxy means a $C_{1-4}$alkoxy bound to a —C(=O)—O— group wherein the term $C_{1-4}$alkoxy is as defined above.

"Halogen", "halo" or "hal" refer to bromo, chloro, iodo or fluoro.

"Nitrile", "cyano" or "carbonitrile" refer to the group —C≡N.

The term $C_{1-4}$alkylcarbonyl refers to a $C_{1-4}$alkyl linked to a carbonyl —C(=O)— group.

The term phenoxy means phenyloxy or a phenyl ether radical.

The term phenylthio means a phenyl linked to the thioether group —S—.

It should be noted that the radical positions on any molecular moiety used in the definitions may be anywhere on such moiety as long as it is chemically stable.

Radicals used in the definitions of any variable herein include all possible isomers unless otherwise indicated.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion, particularly when used on humans and/or mammals. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$— or $^{14}C$-enriched carbon, or the replacement of at least one nitrogen by $^{15}N$-enriched nitrogen are within the scope of this invention.

The compounds of formula (I), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient, is capable of providing (directly or indirectly) a compound as described herein. However, it will be appreciated that non-pharmaceutically acceptable salts, solvates and prodrugs also fall within the scope of the invention since those may be useful in the preparation of pharmaceutically acceptable salts, solvates and prodrugs. The preparation of salts, solvates and prodrugs can be carried out by methods known in the art.

As used herein, the terms "treat", "treating" and "treatment" include the eradication, removal, reversion, alleviation, modification, or control of a disease or condition, such as a cognitive disorder.

As used herein, the terms "prevention", "preventing", "preventive", "prevent" and "prophylaxis" refer to the capacity of a compound of formula (I) to avoid, minimize or difficult the onset or development of a disease or condition, such as a cognitive disorder, before its onset.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as a cognitive disorder. As such, the method of the present invention also includes situations where the condition is completely inhibited, e.g., prevented from happening, or stopped, e.g., terminated, such that the subject no longer experiences the condition. As such, the present method includes both preventing and managing a cognitive disorder.

The term "cognitive disorder," as used herein, means any condition characterized by a deficit in mental activities associated with thinking, learning, or memory. Examples of such disorders include agnosias, amnesias, aphasias, apraxias, deliriums, dementias, and learning disorders.

The cognitive disorder may be (and frequently is) associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington's disease, multiple sclerosis, normal pressure hydrocephalus, organic chronic brain syndrome, Parkinson's disease, Pick disease, progressive supranuclear palsy, or senile dementia (Alzheimer type).

Cognitive disorders may also be associated with other conditions which impair normal functioning of the central nervous system, including psychiatric disorders such as anxiety disorders, dissociative disorders, mood disorders such as bipolar affective disorder, schizophrenia, and somatoform and factitious disorders.

The compounds described here may be used to treat agnosias, amnesias, aphasias, apraxias, deliriums, dementias, learning disorders and other cognitive disorders.

Examples of dementias which may be treated with the methods of the invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia.

The compounds described here may also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

Thus, another aspect of the present invention is a method for the treatment or prophylaxis of cognitive disorders in a mammal wherein a therapeutic amount of a compound of the invention is administered to a patient in need of said treatment.

In a particular embodiment of the present invention the compounds described here may be used to treat patients having a cognitive disorder associated with schizophrenia, bipolar affective disorder, Alzheimer's disease or Parkinson's disease.

In a particular embodiment of the present invention in the compounds of formula (I) or a pharmaceutically acceptable salt, isomer, prodrug or solvate thereof, $R^1$ is hydrogen; $R^2$, $R^3$ and $R^4$ are independently selected from the group consisting of $C_{1-4}$alkoxy, $C_{1-4}$alkylcarbonyloxy, benzyloxy, phenylcarbonyloxy, naphthyl-carbonyloxy, quinolinylcarbonyloxy and isoquinolinylcarbonyloxy; $R^5$ is selected from the group consisting of halogen, nitrile, $C_{1-4}$alkoxy, $C_{1-4}$alkylthio, $C_{1-4}$alkyl, phenyl, phenoxy, phenylthio and trifluoromethyl and $R^6$ is selected from the group consisting of hydrogen, fluor and methyl.

In a particular embodiment, $R^2$ and $R^4$ are independently selected from the group consisting of hydrogen, halogen, trifluoromethyl and $C_{1-4}$alkoxy In another particular embodiment, $R^2$ is selected from the group consisting of hydrogen and methoxy and $R^4$ is selected from the group consisting of fluor, trifluoromethyl and methoxy.

In another particular embodiment, $R^5$ is fluor.

In a particular embodiment, $R^2$ and $R^4$ are independently selected from the group consisting of $C_{1-4}$alkoxy, $C_{1-4}$alkylcarbonyloxy and benzyloxy.

In a particular embodiment, $R^2$ and $R^4$ are methoxy.

In another embodiment, $R^3$ is a benzyloxy.

In another embodiment $R^1$ is hydrogen.

In another embodiment, $R^5$ is selected from fluor, methoxy, methylthio and phenyl, preferably fluor.

In another embodiment, $R^6$ is hydrogen or fluor.

In additional preferred embodiments, the preferences described above for the different substituents are combined.

The present invention is also directed to such combinations of preferred substitutions in the formulae above.

Particular individual compounds of the invention falling under formula (I) include the compounds listed below:
(S)-1-((2S,4R)-1-(4-(benzyloxy)-3,5-dimethoxybenzoyl)-4-methoxypyrrolidine-2-carbonyl)pyrrolidine-2-carbonitrile
(S)-1-((2S,4R)-1-(4-(benzyloxy)-3,5-dimethoxybenzoyl)-4-fluoropyrrolidine-2-carbonyl)pyrrolidine-2-carbonitrile
(S)-1-((2S,4S)-1-(4-(benzyloxy)-3,5-dimethoxybenzoyl)-4-phenylpyrrolidine-2-carbonyl)pyrrolidine-2-carbonitrile
(S)-1-((2S)-1-(4-(benzyloxy)-3,5-dimethoxybenzoyl)-4,4-difluoropyrrolidine-2-carbonyl)pyrrolidine-2-carbonitrile
(S)-1-((2S,4S)-1-(4-(benzyloxy)-3,5-dimethoxybenzoyl)-4-(methylthio)pyrrolidine-2-carbonyl)pyrrolidine-2-carbonitrile
(S)-1-((2S,4S)-1-(4-(benzyloxy)-3,5-dimethoxybenzoyl)-4-methylpyrrolidine-2-carbonyl)pyrrolidine-2-carbonitrile
(S)-1-((2S,4R)-1-(4-(benzyloxy)-3,5-dimethoxybenzoyl)-4-cyanopyrrolidine-2-carbonyl)pyrrolidine-2-carbonitrile
(S)-1-((2S,4S)-1-(4-(benzyloxy)-3,5-dimethoxybenzoyl)-4-(trifluoromethyl)-pyrrolidine-2-carbonyl)pyrrolidine-2-carbonitrile
(S)-1-((2S,4R)-1-(4-(benzyloxy)-3,5-dimethoxybenzoyl)-4-(tert-butoxy) pyrrolidine-2-carbonyl)pyrrolidine-2-carbonitrile
(S)-1-((2S,4R)-1-(4-(benzyloxy)-3,5-dimethoxybenzoyl)-4-acetoxypyrrolidine-2-carbonyl)pyrrolidine-2-carbonitrile
(S)-1-((2S)-1-(4-acetoxy-3,5-dimethoxybenzoyl)-4,4-difluoropyrrolidine-2-carbonyl)pyrrolidine-2-carbonitrile
(S)-1-((2S)-1-(4-benzoyloxy-3,5-dimethoxybenzoyl)-4,4-difluoropyrrolidine-2-carbonyl)pyrrolidine-2-carbonitrile
(S)-1-((2S)-1-(3,4-dibenzyloxy-5-methoxybenzoyl)-4,4-difluoropyrrolidine-2-carbonyl)pyrrolidine-2-carbonitrile
(S)-1-((2S)-1-(3,4-dibenzoyloxy-5-methoxybenzoyl)-4,4-difluoropyrrolidine-2-carbonyl)pyrrolidine-2-carbonitrile
(S)-1-((2S)-1-(3-acetoxy-4,5-dimethoxybenzoyl)-4,4-difluoropyrrolidine-2-carbonyl)pyrrolidine-2-carbonitrile
(S)-1-((2S)-1-(3-pivaloyloxy-4,5-dimethoxybenzoyl)-4,4-difluoropyrrolidine-2-carbonyl)pyrrolidine-2-carbonitrile
(S)-1-((S)-1-(4-(benzyloxy)benzoyl)-4,4-difluoropyrrolidine-2-carbonyl)pyrrolidine-2-carbonitrile
(S)-1-((S)-1-(3-(benzyloxy)benzoyl)-4,4-difluoropyrrolidine-2-carbonyl)pyrrolidine-2-carbonitrile
(S)-1-((S)-1-(2-(benzyloxy)benzoyl)-4,4-difluoropyrrolidine-2-carbonyl)pyrrolidine-2-carbonitrile
(S)-1-((S)-1-(4-(benzyloxy)-3-(trifluoromethyl)benzoyl)-4,4-difluoropyrrolidine-2-carbonyl)pyrrolidine-2-carbonitrile
(S)-1-((S)-1-(4-(benzyloxy)-3-fluorobenzoyl)-4,4-difluoropyrrolidine-2-carbonyl)pyrrolidine-2-carbonitrile
or a pharmaceutically acceptable salt, isomer, prodrug or solvate thereof.

The compounds of formula (I) defined above can be obtained by available synthetic procedures as illustrated by the following general schemes:

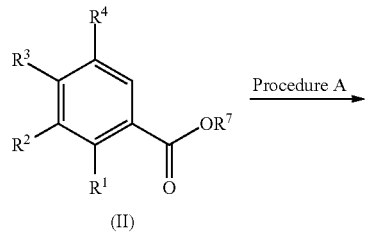

(II)

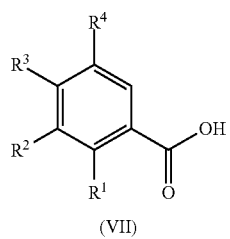
(VII)
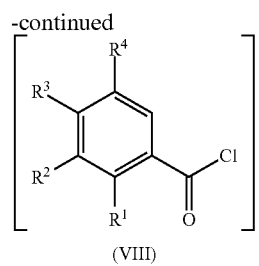
(VIII)
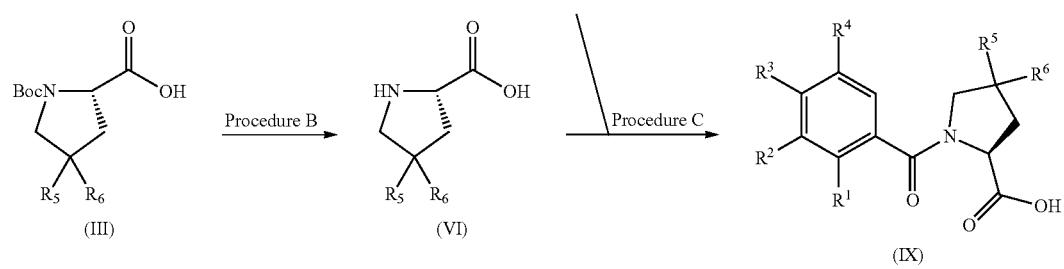
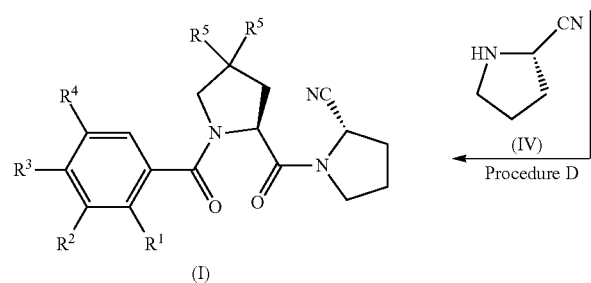
Detailed Scheme for Procedure E
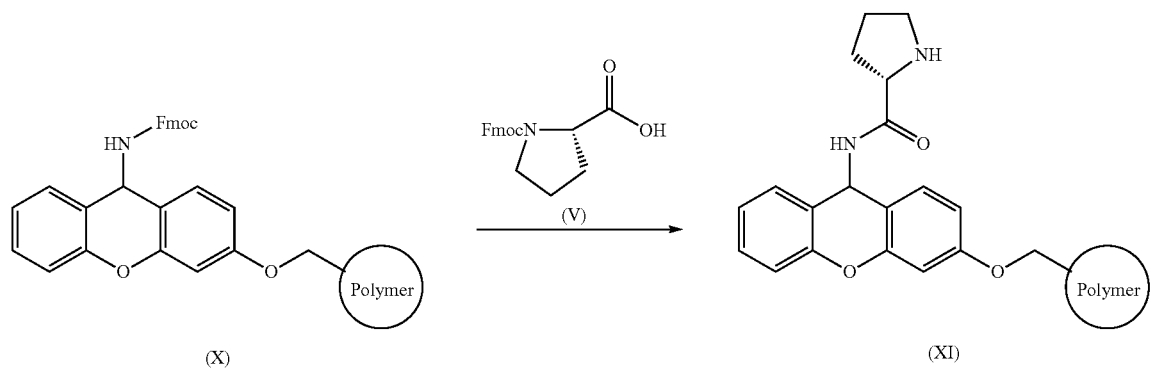

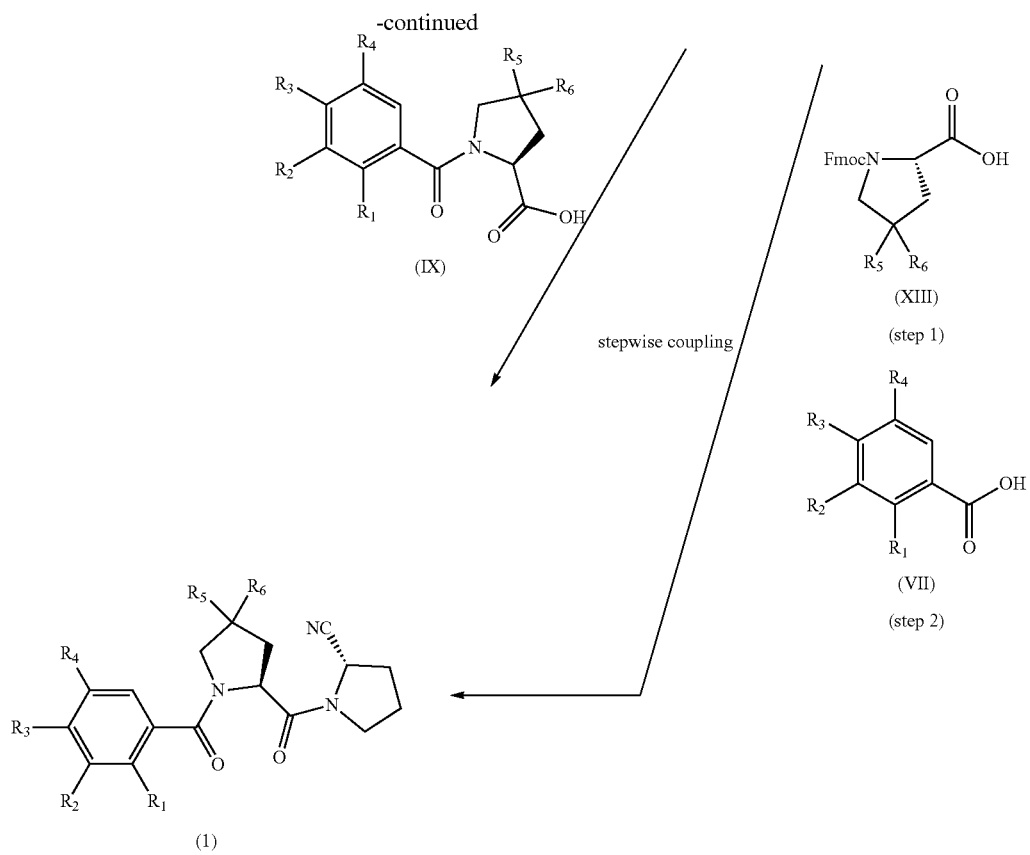

In a first step the ester of formula (II) is dissolved or suspended in a polar organic solvent (preferably a protic polar organic solvent) such as ethanol (EtOH) or methanol or a mixture of polar organic solvents. An aqueous base solution is added and the hydrolytic reaction is performed by maintaining the mixture, typically under reflux, at a temperature comprised between room temperature and the reflux temperature of the solvent mixture until completion of the hydrolysis, typically for a period of 0.5 to 4 hours, preferably 1-2 hours. The base solution is preferably of inorganic nature, such as a dillute alkali, for example NaOH. Then the reaction mixture is left to reach room temperature and, preferably, concentrated to approximately a fifth of the reaction volume. The reaction mixture is then slowly added to an acid solution such as a 1M HCl solution to effect neutralization, while cooled in an ice bath. If acidification leads to precipitation, the solid is filtered and washed with water, providing the product of formula (VII). If no precipitate is obtained, the resulting solution is extracted several times with an appropriate organic solvent such as ethyl acetate, the organic phase is dried and evaporated. The crude product of formula (VII) is purified by flash chromatography.

Deprotection of the amine of formula (III) is achieved under mild acidic conditions, such as addition onto a hydrogen chloride solution in an organic solvent such as dioxane, or with a TFA/DCM mixture, at low temperature ranging from 0° C. to room temperature. The reaction is stirred at room temperature for 1-3 hours. The solvent is then evaporated to dryness, to give the hydrochloride salt or the trifluoroacetate salt of the amine of formula (VI), depending on the acid used.

The compound of formula (IX) is prepared from the carboxylic acid of formula (VII) and amine of formula (VI) under Schotten-Baumann conditions. Thus, a chlorinating agent such as oxalyl chloride is added to a solution of the carboxylic acid of formula (VII) in an organic solvent such as toluene. The reaction is stirred at a temperature between 50° C. and 80° C. for 1 to 2 hours to allow for the formation of the carboxylic acid chloride of formula (VIII). After evaporation of the solvent, the resulting crude is solubilized in an organic solvent such as THF and added to an aqueous basic solution of the amine of formula (VI), typically an aqueous NaOH solution of the amine of formula (VI), at a low temperature such as 0° C. The reaction mixture is stirred at the low temperature for 1 to 2 hours and at room temperature during 2 to 4 hours. Then, the solvent is evaporated and the remaining aqueous fraction is adjusted to acid pH (3-4) by addition of a HCl solution and extracted with ethyl acetate. The organic phase is washed with brine, dried, filtered and evaporated. The crude product is purified by flash chromatography when necessary.

The product of formula (IX) is then coupled to (S)-pyrrolidine-2-carbonitrile of formula (IV) in the presence of a base, such as a N,N-diisopropylethylamine (DIEA), and aided by a coupling reagent, such as a carbodiimide. In particular, the compound of formula (IX) is dissolved in an aprotic organic solvent such as dichloromethane and added to a carbodiimide, for example a solid-supported carbodiimide such as N-cyclohexylcarbodiimide, N'-methyl polystyrene, together with DIEA. After 5 min, (S)-pyrrolidine-2-carbonitrile of formula (IV) and extra DIEA are added. The reaction is stirred at room temperature for 8 to 16 hours. Then, the reaction mixture is filtered and the remaining solid is washed with the aprotic organic solvent. The filtrate is evaporated to dryness. The crude product is then purified by preparative RP-HPLC.

Alternatively, the compounds of formula (I) may be prepared as illustrated in Scheme E and described below:

An amine-functionalised resin such as Sieber amide resin of formula (X) is placed in a syringe fitted with a polyethylene porous disk. The resin is swelled by washes with appropriate organic solvents such as dichloromethane (DCM) and dimethylformamide (DMF). When the amine group of the resin is protected (i.e. in the case of Sieber amide resin), removal of the protecting group (such as a fluorenylmethoxycarbonyl (Fmoc) protecting group) is achieved by treatment with an amine base solution such as a piperidine solution in DMF.

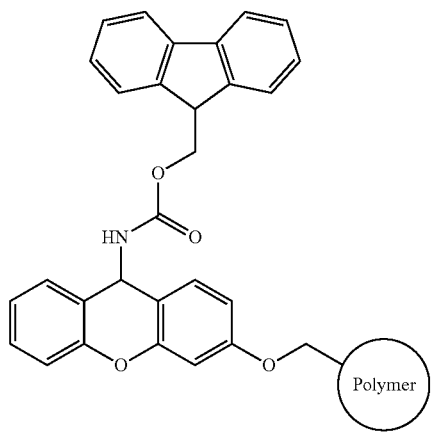

Following removal of the protecting group from the resin, Fmoc-protected L-Proline of formula (V) is attached to the resin using an activating agent such as a triazole (i.e. TBTU) and an amine base such as DIEA in an appropriate organic solvent such as DMF. The mixture is stirred during 1 to 2 hours. After filtration and washing, the extent of the coupling may be monitored using the Kaiser test, re-coupling is performed when required. Fmoc is removed to yield product of formula (XI) by a treatment with an amine base solution such as a piperidine solution in DMF and/or a mixture of piperidine/DBU/toluene/DMF. Fmoc removal may be assessed using the p-nitrophenyl ester NF31 test.

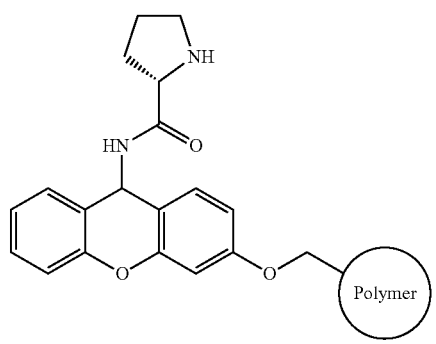

The product of formula (XI) is coupled to the product of formula (IX) to yield the product of formula (XII) using an activating agent such as PyBOP, in the presence or in the absence of an additive such as HOAt, and an amine base such as DIEA in an appropriate organic solvent such as DMF. The mixture is stirred manually during the total reaction time of 1 to 2 hours. A systematic re-coupling is done using the same amounts and time. The extent of the coupling may be monitored using the p-nitrophenyl ester NF31 test.

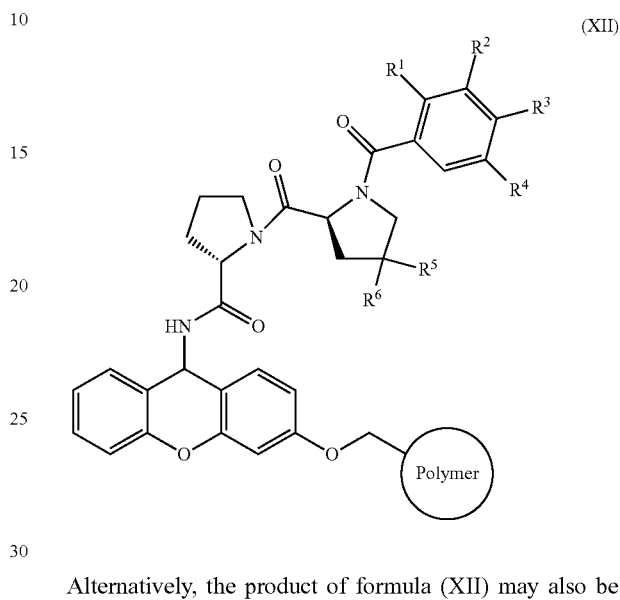

Alternatively, the product of formula (XII) may also be obtained by stepwise coupling of product (XI) first to compound of formula (XIII), followed by the removal of the Fmoc protecting group and then coupling with compound of formula (VII).

The product of formula (XII), thoroughly washed with an appropriate organic solvent such as DCM and dried, is transferred to a flask, to which trifluoroacetic anhydride and pyridine are added in a small amount of an organic solvent. The mixture is kept at a temperature of 20 to 40° C. for 8 to 16 hours. Then, the reaction mixture is filtered and the resin is washed with the same organic solvent. The filtrates are collected and the solvent is evaporated to dryness. The resulting crude is dissolved in an appropriate solvent such as ethyl acetate and washed with saturated NaHCO$_3$ solution and a 5% aq. KHSO$_4$ solution. The organic phase is dried, filtered, and evaporated. The crude is taken up in H$_2$O:CH$_3$CN and lyophilized to yield the peptide nitrile of formula (I).

Alternatively, the peptidyl-resin of formula (XII) may be treated with a mixture of TFA/H$_2$O/TIS during 1-2 hours. Then, the resin is filtered and washed with TFA, the filtrates are collected and the solvent is evaporated to dryness. The crude is resuspended in a mixture of H$_2$O:CH$_3$CN and lyophilized. The resulting crude peptide amide is taken up in an appropriate organic solvent such as DCM and converted to the nitrile for example in the presence of phosphorus pentoxide, titanium tetrachloride, thionyl chloride, trifluoroacetic anhydride/pyridine or triphenylphosphine/carbontetrachloride. The mixture is kept at room temperature for 8 to 16 hours, the solvent is evaporated and the residue taken up in ethyl acetate. The organic solution is subsequently washed with aq. KHSO$_4$ solution and aq. NaHCO$_3$ solution. Drying and evaporation of the organic phase yields the peptide nitrile of formula (I).

The crude product is purified by RP-HPLC.

Where the above described processes for the preparation of compounds of the invention give rise to mixtures of stereoisomers, these isomers may be separated by conventional techniques such as preparative chromatography. If there are chiral centers, the compounds may be prepared in racemic form, or individual enantiomers may be prepared either by enantiospecific synthesis or by resolution.

The compounds of formulae (II), (III), (IV) and (V), as well as some of the compounds of formula (VII), used as starting products are either commercially available and may also be prepared using methods well known to the expert in the field.

Thus, in one aspect the present invention provides for processes for the preparation of a compound of formula (I) or a pharmaceutically acceptable salt, isomer, prodrug or solvate thereof.

In one embodiment the process comprises the steps of:

a) reacting a compound of formula (IX):

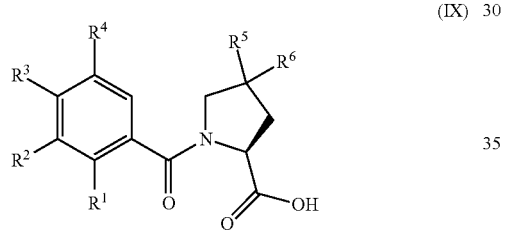

(IX)

in which $R^1$, $R^2$, $R^3$, $R^4$, $R^5$ and $R^6$ are as defined above in formula (I), with a compound of formula (XI):

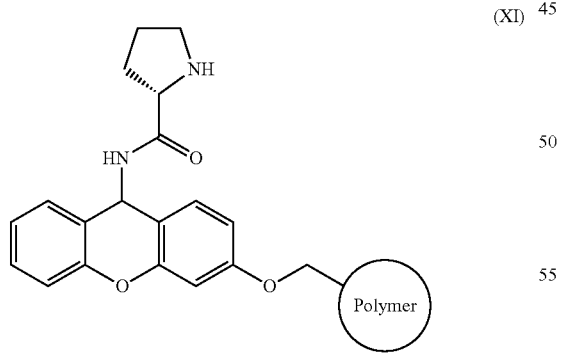

(XI)

wherein polymer stands for a polymer which is inert under the reaction conditions of the synthetic method herein-disclosed and insoluble but swellable in the solvents herein-employed such as low cross-linked polystyrene and polyethyleneglycol-grafted polystyrene polymers.

to yield a compound of formula (XII);

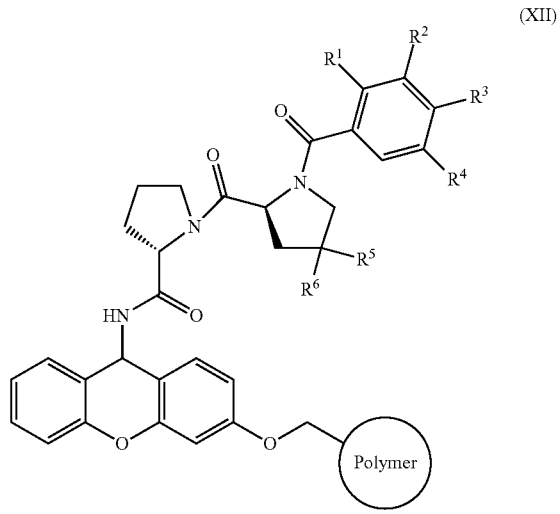

(XII)

b) hydrolising the compound of formula (XII) to yield the compound of formula (XIV)

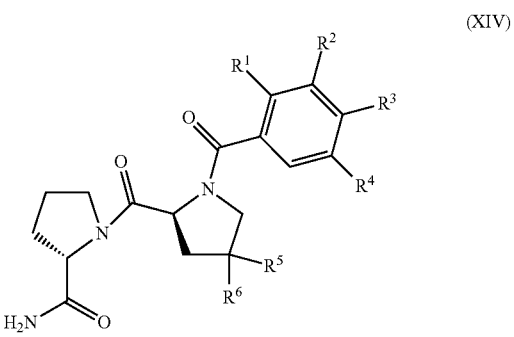

(XIV)

and c) subjecting the compound of formula (XIV) to conditions capable of transforming a carboxamide group into a nitrile group to yield the compound of formula (I);

wherein steps b) and c) may be performed separately or in a one pot reaction.

In another embodiment of the present invention the process for the preparation of a compound of formula (I) or a pharmaceutically acceptable salt, isomer, prodrug or solvate thereof, comprises the steps of:

a) reacting a compound of formula (IX):

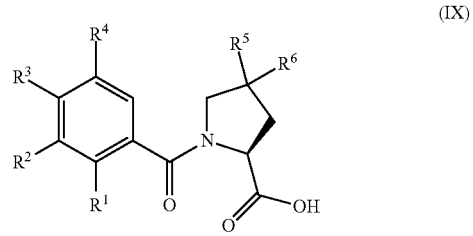

(IX)

in which $R^1$, $R^2$, $R^3$, $R^4$, $R^5$ and $R^6$ are as defined above in formula (I), with a compound of formula (IV)

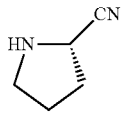
(IV)

In still another embodiment the process comprises the steps of:
a) reacting a compound of formula (XI):

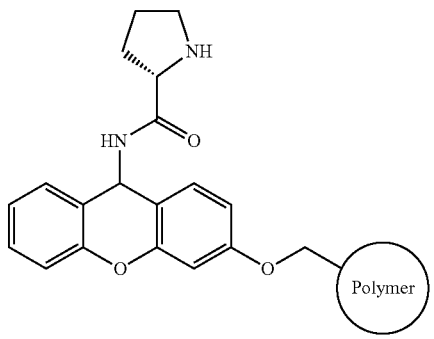
(XI)

wherein polymer stands for a polymer which is inert under the reaction conditions of the synthetic method herein-disclosed and insoluble but swellable in the solvents herein-employed such as low cross-linked polystyrene and polyethyleneglycol-grafted polystyrene polymers.
with a compound of formula (XIII):

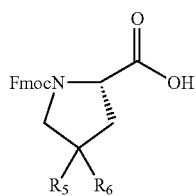
(XIII)

in which $R^5$ and $R^6$ are as defined above in formula (I)
b) removing the Fmoc protecting group
c) reacting with a compound of formula (VII);

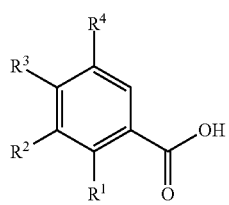
(VII)

in which $R^1$, $R^2$, $R^3$ and $R^4$ are as defined above in formula (I)
d) hydrolising the resulting product from the supporting polymer to yield the compound of formula (I)

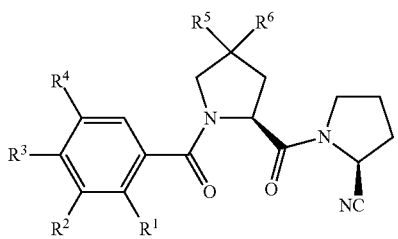
(I)

in which $R^1$, $R^2$, $R^3$, $R^4$, $R^5$ and $R^6$ are as defined above.

It has been found that the compounds of general formula (I) are useful in the treatment of cognitive disorders, in particular cognitive disorders associated with other diseases or conditions of the central nervous system.

In a particular embodiment of the present invention, the cognitive disorder is a cognitive disorder associated with a disease selected from the group consisting of schizophrenia, bipolar affective disorder, Alzheimer's disease and Parkinson's disease.

The present invention further provides medicaments or pharmaceutical compositions comprising a compound of this invention, or a pharmaceutically salt, derivative, prodrug or stereoisomer thereof together with a pharmaceutically acceptable carrier, adjuvant, or vehicle, for administration to a patient.

The auxiliary materials or additives of a pharmaceutical composition according to the present invention can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The medicament or pharmaceutical composition according to the present invention may be in any form suitable for the application to humans and/or animals, preferably humans including infants, children and adults and can be produced by standard procedures known to those skilled in the art. Therefore, the formulation in accordance with the invention may be adapted for topical or systemic application, particularly for dermal, transdermal, subcutaneous, intramuscular, infra-articular, intraperitoneal, intravenous, intra-arterial, intravesical, intraosseous, intracavernosal, intranasal, pulmonary, buccal, sublingual, ocular, intravitreal, percutaneous, rectal, vaginal, oral, epidural, intrathecal, intraventricular, intracerebral, intracerebroventricular, intracisternal, intraspinal, perispinal, intracranial, delivery via needles or catheters with or without pump devices, or other application routes.

In an embodiment the pharmaceutical compositions are in oral form, either solid or liquid. Suitable dose forms for oral administration may be tablets, pills, caplets, gel caps, chewing gums, capsules, granules, drops, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

In another embodiment the pharmaceutical compositions are in the form of products for non-parenteral intranasal administration, preferably in the form of products for intranasal administration. Typically intranasal administration is carried out by using nasal sprays, squeeze bottles, and liquid droppers as delivery devices. To be used with these devices, the pharmaceutical compositions are advantageously liquid solutions or suspensions of the compounds of the invention.

The compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or reconstitutable dry preparations, aerosols or sprays in the appropriate unit dosage form. Adequate excipients can be used, such as bulking agents, buffering agents or surfactants.

The composition of the invention may be formulated as deposits in dissolved form or in patches, for percutaneous application.

Skin applications include ointments, gels, creams, lotions, suspensions or emulsions.

Suitable form of rectal application is by means of suppositories.

The mentioned formulations will be prepared using standard methods such as those described or referred to in the Spanish and US Pharmacopoeias and similar reference texts.

In one embodiment of the invention it is preferred that compound of formula (I) is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of disease or condition being treated. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. Active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Particularly, the combination of at least one compound of formula (I) and at least one another drug may be formulated for its simultaneous, separate or sequential administration, with at least a pharmaceutically acceptable carrier, additive, adjuvant or vehicle. This has the implication that the combination of the compound of formula (I) and the other drug may be administered:
  a) As a combination that is being part of the same medicament formulation, both being then administered always simultaneously.
  b) As a combination of two units, each with one of them giving rise to the possibility of simultaneous, sequential or separate administration. In a particular embodiment, the compound of formula (I) is independently administered from the other drug (i.e. in two units) but at the same time. In another particular embodiment, the compound of formula (I) is administered first, and then the other drug is separately or sequentially administered. In yet another particular embodiment, the other drug is administered first, and then the compound of formula (I) is administered, separately or sequentially, as defined.

In the context of the present invention, the following acronyms and abbreviations have been used, the meaning detailed below:
  AcOEt Ethyl acetate
  AcSDKP N-acetyl-seryl-aspartyl-lysyl-proline
  AD Alzheimer's disease
  BBB Blood-Brain Barrier
  Boc tert-Butoxycarbonyl
  BSA Bovine serum albumin
  DBU 1,8-Diazabicyclo[5.4.0]undec-7-ene
  DCM Dichloromethane
  DIEA N,N'-Diisopropylethylamine
  DMF Dimethylformamide
  DMSO Dimethylsulfoxide
  DPPIV Dipeptidyl peptidase IV
  EtOH Ethanol
  Fmoc 9-Fluorenylmethoxycarbonyl
  FPLC Fast protein liquid chromatography
  HOAt 1-Hydroxy-7-azabenzotriazole
  IP3 Inositol triphosphate
  IPTG Isopropyl β-D-1-thiogalactopyranoside
  LB Lysogeny broth
  MALDI-TOF Matrix-assisted laser desorption/ionization-time-of-flight
  MK-801 Dizocilpine (INN)
  MS Multiple sclerosis
  OD Optical density
  PAMPA Parallel artificial membrane permeability assay
  PBS Phosphate buffered saline
  PC Phosphatidylcholine
  PE Phosphatidyletanolamine
  pETM10 Plasmid pETM10
  PI Phosphatidylinositol
  POP Prolyl oligopeptidase
  hPOP human Prolyl oligopeptidase
  PREP Prolyl endopeptidase (please note that POP and PREP are synonyms)
  PS Phosphatidylserine
  PyBOP (Benzotriazol-1-yloxy)tripyrrolidinophosphonium hexafluorophosphate
  RP-HPLC Reverse phase high performance liquid cromatography
  SD Standard deviation
  SDS-PAGE Sodium dodecyl sulfate polyacrylamide gel electrophoresis
  TBTU O-(Benzotriazol-1-yl)-N,N,N',N'-tetramethyluronium tetrafluoroborate
  TFA Trifluoroacetic acid
  THF Tetrahydrofuran
  TIS Triisopropylsilane
  Tris Tris(hydroxymethyl)aminomethane
  Tβ4 Thymosin beta-4 protein
  Z-G-P-AMC (N-Benzyloxycarbonyl-Gly-Pro-methyl-coumarinyl-7-amide)

The following examples are merely illustrative of certain embodiments of the invention and cannot be considered as restricting it in any way.

EXAMPLES

Specific Synthetic Conditions Used for the Preparations Described in the Examples Procedure A: Hydrolysis of Ester of Formula (II) to the Carboxylic Acid of Formula (VII)

The ester of formula (II) (1 mmol) is solubilized in 95% EtOH. NaOH (3.7 mmol) is added and the reaction is maintained at reflux for approximately 2 hours. Then it is left to reach room temperature. The reaction mixture is concentrated to approx. 15-20 mL and then this solution is slowly added onto a 1M HCl solution, while cooled in an ice bath. A white solid precipitates, which is collected by filtration, washed with water and dried well before the next synthetic step. In the case that no precipitate appears, the resulting solution is extracted with AcOEt (3×), the organic phase is dried and evaporated. The crude product is purified by flash chromatography, if needed.

Procedure B: Deprotection of a Boc Protected Amine of Formula (III) to Yield the Amine of Formula (VI)

The Boc protected amine of formula (III) (1 mmol) is slowly added onto 4M HCl in dioxane (20 ml) at 0° C. The reaction is stirred at room temperature for 2 hours. The solvent is then evaporated to dryness, to give the hydrochloride salt of the amine of formula (VI).

Procedure C: Coupling of an amine of formula (VI) to a carboxylic acid of formula (VII) through formation of the carboxylic acid chloride of formula (VIII).

Oxalyl chloride (1.5 mmol) is added to a solution of the carboxylic acid of formula (VII) (1 mmol) in toluene (5 ml). The reaction is stirred at 50° C. for 1.5 hours to allow for the formation of the carboxylic acid chloride of formula (VIII). After evaporation of the solvent, the resulting crude is solubilized in THF and added to an aqueous NaOH solution of the amine of formula (VI) (1.1 mmol) at 0° C. The reaction mixture is stirred at 0° C. for 1.5 hours and at room temperature during 3 hours. Then, THF is evaporated and the remaining aqueous fraction is adjusted to acid pH (3-4) by addition of 1M HCl solution and extracted with AcOEt. The organic phase is washed with brine, dried, filtered and evaporated. The crude product of formula (IX) is purified by flash chromatography when necessary.

Procedure D: Coupling of the Product of Formula (IX) to (S)-Pyrrolidine-2-Carbonitrile of Formula (IV) in Solution The product of formula (IX) (1.2 mmol) is dissolved in DCM and added to N-Cyclohexylcarbodiimide, N'-methyl polystyrene (3 mmol), together with DIEA (1 mmol). After 5 min, (S)-pyrrolidine-2-carbonitrile of formula (IV) (1 mmol) and DIEA (1 mmol) are added. The reaction is stirred at room temperature overnight. Then, the reaction mixture is filtered and the remaining solid is washed with DCM. The filtrate is evaporated to dryness. The crude product is then purified by preparative RP-HPLC.

Procedure E: General Procedure for Synthesis on Solid-Phase:

Swelling/conditioning of the resin: Sieber amide resin of formula (X) (1 eq) is placed in a syringe fitted with a polyethylene porous disk. The resin is swelled by washes with DCM and DMF. Removal of the fluorenylmethoxycarbonyl (Fmoc) protecting group is achieved by treatments with a 20% piperidine solution in DMF.

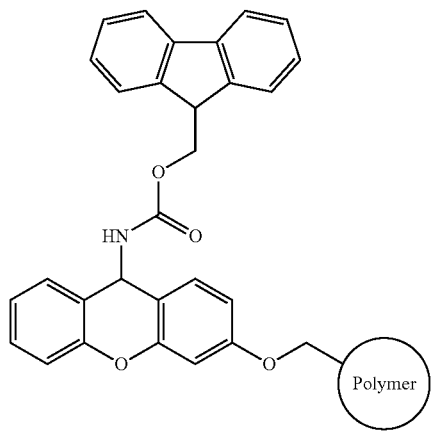

(X)

Then, Fmoc-protected L-Proline of formula (V) (4 eq) is attached to the resin using TBTU (4 eq) and DIEA (8 eq) in DMF. The mixture is intermittently stirred manually during 90 min. After filtration and washing, the extent of the coupling is monitored using the Kaiser test, re-coupling is performed when required. Fmoc is removed to yield product of formula (XI) by a treatment with a 20% piperidine solution in DMF and subsequently with a piperidine/DBU/toluene/DMF (20:5:5:70) solution. Fmoc removal is assessed using the p-nitrophenyl ester NF31 test (described in Madder, A. et al., *Eur. J. Org. Chem.* 1999; (11):2787-91).

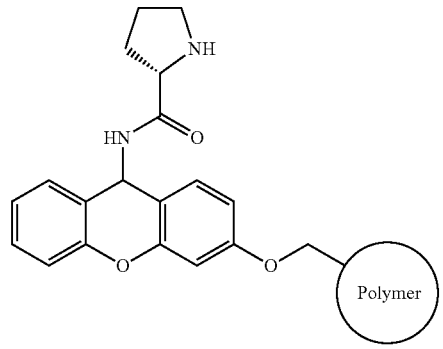

(XI)

The product of formula (IX) (2 eq) is coupled to the product of formula (XI) to yield the product of formula (XII) using PyBOP (2 eq), HOAt (6 eq) and DIEA (6 eq) in DMF. The mixture is intermittently stirred manually during the total reaction time, 90 min. A systematic re-coupling is done using the same amounts and time. The extent of the coupling is monitored using the p-nitrophenyl ester NF31 test.

Alternatively, the product of formula (XIII) (4 eq) is coupled to the product of formula (XI) using PyBOP (4 eq), HGAt (12 eq) and DIEA (12 eq) in DMF. The mixture is intermittently stirred manually during the total reaction time, 90 min. The extent of the coupling is monitored using the p-nitrophenyl ester NF31 test, and a re-coupling is done if necessary. The Fmoc group is removed by a treatment with a 20% piperidine solution in DMF and a treatment with a piperidine/DBU/toluene/DMF (20:5:5:70) solution. Subsequently, the product of formula (VII) (4 eq) is incorporated, using PyBOP (4 eq), HOAt (12 eq) and DIEA (12 eq) in DMF, to obtain the product of formula (XII). The mixture is intermittently stirred manually during the total reaction time, 90 min. The extent of the coupling is monitored using the p-nitrophenyl ester NF31 test, and a re-coupling is done if necessary.

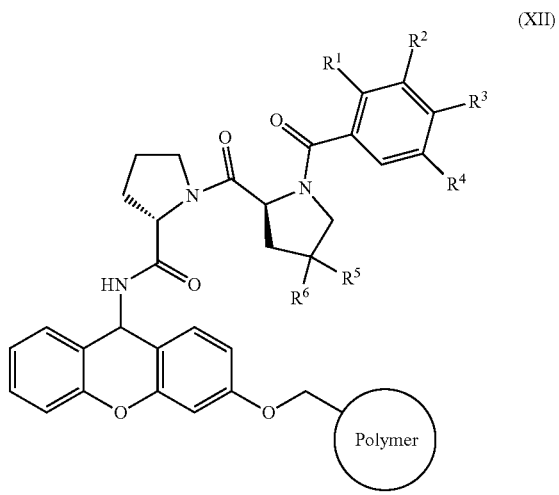

The product of formula (XII), thoroughly washed with DCM and dried, is transferred to a round bottom flask, and trifluoroacetic anhydride (5 eq) and pyridine (10 eq) in DCM (approx. 2 mL/100 mg) are added. The mixture is kept at room temperature overnight. Then, the reaction mixture is filtered and the resin is washed with DCM. The filtrates are collected and the solvent is evaporated to dryness. The resulting crude is dissolved in AcOEt and washed with saturated $NaHCO_3$ solution and a 5% aq. $KHSO_4$ solution. The organic phase is dried, filtered, and evaporated. The crude is taken up in $H_2O:CH_3CN$ (1:1) and lyophilized to yield the peptide nitrile of formula (I).

Alternatively, the peptidyl-resin of formula (XII) may be treated with a mixture of $TFA/H_2O/TIS$ (95:2.5:2.5, approx. 2-5 mL/100 mg) during 1-2 hours. Then, the resin is filtered and washed with TFA, the filtrates are collected and the solvent is evaporated to dryness. The crude is resuspended in a mixture of $H_2O:CH_3CN$ (1:1) and lyophilized. The resulting crude peptide amide is taken up in DCM and trifluoroacetic anhydride (5 eq) and pyridine (10 eq) are added. The mixture is kept at room temperature overnight, the solvent is evaporated and the residue taken up in AcOEt. The organic solution is subsequently washed with aq. 5% $KHSO_4$ solution and aq. 10% $NaHCO_3$ solution. Drying and evaporation of the organic phase yield the peptide nitrile of formula (I).

The crude product is purified by RP-HPLC.

Synthesis of Intermediate Compounds:

Intermediate 1: 4-benzyloxy-3,5-dimethoxybenzoic Acid

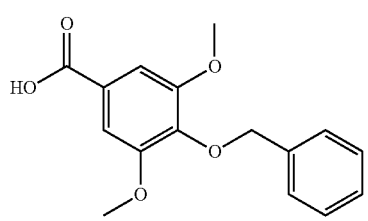 [SMILES: COc1cc(C(=O)O)cc(OC)c1OCc1ccccc1]

Methyl 3,5-dimethoxy-4-hydroxybenzoate (2.0 g, 9.4 mmol), potassium carbonate (3.2 g, 22.6 mmol) and potassium iodide (500 mg, 3.0 mmol) are introduced in a round-bottom flask. Acetone (200 mL) is added. The reaction is stirred at room temperature for 30 minutes. Then, benzyl chloride (4.3 mL, 37.7 mmol) is added to the reaction mixture and stirring is maintained at reflux during 8 hours. Afterwards, the reaction is left to cool to room temperature. Water is added and three extractions with diethyl ether are performed, the organic extract is washed with brine, dried and evaporated. The crude product is purified by flash chromatography, yielding 1.7 g (5.7 mmol). Subsequently, hydrolysis of the methyl ester is performed following Procedure A described above, to give 4-benzyloxy-3,5-dimethoxybenzoic acid (2.4 g, 7.9 mmol).

Intermediate 2: (2S,4R)-4-methoxypyrrolidine-2-carboxylic Acid

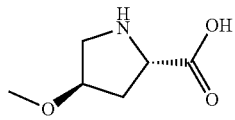

Starting from commercially available (2S,4R)-1-(tert-butoxycarbonyl)-4-methoxypyrrolidine-2-carboxylic acid (221 mg, 1.5 mmol), the product is obtained in quantitative yield as the hydrochloride salt following Procedure B described above and used without further purification.

Intermediate 3: (S)-4,4-difluoropyrrolidine-2-carboxylic Acid

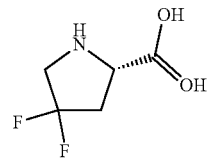

Starting from commercially available (S)-1-(tert-butoxycarbonyl)-4,4-difluoropyrrolidine-2-carboxylic acid (150 mg, 1.0 mmol), the product is obtained in quantitative yield as the hydrochloride salt following Procedure B described above and used without further purification.

Intermediate 4: (2S,4S)-4-(methylthio)pyrrolidine-2-carboxylic Acid

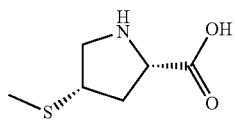

Starting from commercially available (2S,4S)-1-(tert-butoxycarbonyl)-4-methylthio-pyrrolidine-2-carboxylic acid (310 mg, 1.93 mmol), the product is obtained in quantitative yield as the hydrochloride salt following Procedure B described above and used without further purification.

Intermediate 5: (2S,4S)-4-methylpyrrolidine-2-carboxylic Acid

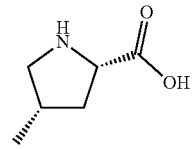

Starting from commercially available (2S,4S)-1-(tert-butoxycarbonyl)-4-methylpyrrolidine-2-carboxylic acid (500 mg, 2.18 mmol), the product is obtained in quantitative yield as the hydrochloride salt following Procedure B described above and used without further purification.

Intermediate 6: (2S,4R)-4-acetoxypyrrolidine-2-carboxylic Acid

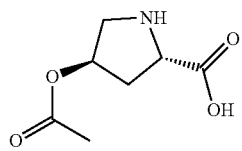

Commercially available trans-L-hydroxyproline (500 mg, 3.81 mmol) is dissolved in 6N hydrochloric acid (1 mL). Glacial acetic acid (1 mL) is added, and the solution is cooled to 0° C. in an ice bath. Acetyl chloride (10 mL) is then added slowly. After a few minutes, the product is obtained through precipitation, which is helped by addition of ether. The compound (626 mg, 2.98 mmol), in the form of hydrochloride salt, is isolated through nitration, washed with ether, dried and used directly in the next step.

Intermediate 7: (2S,4R)-1-(4-(benzyloxy)-3,5-dimethoxybenzoyl)-4-methoxy-pyrrolidine-2-carboxylic Acid

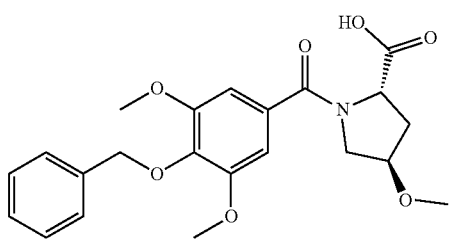 [SMILES: COc1cc(C(=O)N2C[C@H](OC)C[C@H]2C(=O)O)cc(OC)c1OCc1ccccc1]

Prepared following Procedure C described above from Intermediate 1 (4-benzyloxy-3,5-dimethoxybenzoic acid) (425 mg, 1.5 mmol) and Intermediate 2 ((2S,4R)-4-methoxypyrrolidine-2-carboxylic acid) (1.5 mmol). Purification by flash chromatography affords the desired product (428 mg, 1.0 mmol).

Intermediate 8: (2S,4R)-1-(4-(benzyloxy)-3,5-dimethoxybenzoyl)-4-fluoropyrrolidine-2-carboxylic Acid

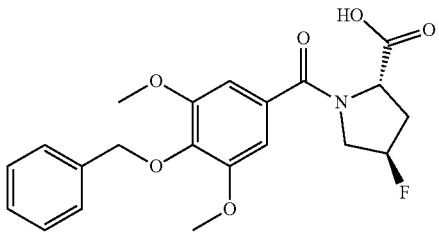 [SMILES: COc1cc(C(=O)N2C[C@H](F)C[C@H]2C(=O)O)cc(OC)c1OCc1ccccc1]

Prepared following Procedure C described above from Intermediate 1 (4-benzyloxy-3,5-dimethoxybenzoic acid) (714 mg, 2.5 mmol) and commercially available (2S,4R)-4-fluoropyrrolidine-2-carboxylic acid (363 mg, 2.7 mmol). Purification by flash chromatography affords the desired product (670 mg, 1.7 mmol).

Intermediate 9: (2S,4S)-1-(4-(benzyloxy)-3,5-dimethoxybenzoyl)-4-phenylpyrrolidine-2-carboxylic Acid

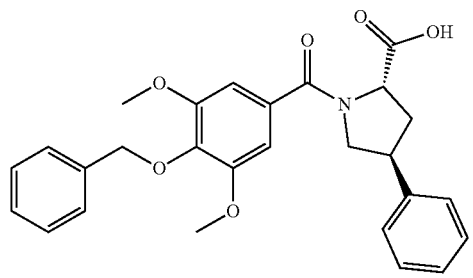 [SMILES: COc1cc(C(=O)N2C[C@H](c3ccccc3)C[C@H]2C(=O)O)cc(OC)c1OCc1ccccc1]

Prepared following Procedure C described above from Intermediate 1 (4-benzyloxy-3,5-dimethoxybenzoic acid) (700 mg, 2.4 mmol) and commercially available (2S,4S)-4-phenylpyrrolidine-2-carboxylic acid (608 mg, 2.7 mmol). Purification by flash chromatography affords the desired product (700 mg, 1.5 mmol).

Intermediate 10: (S)-1-(4-(benzyloxy)-3,5-dimethoxybenzoyl)-4,4-difluoropyrrolidine-2-carboxylic Acid

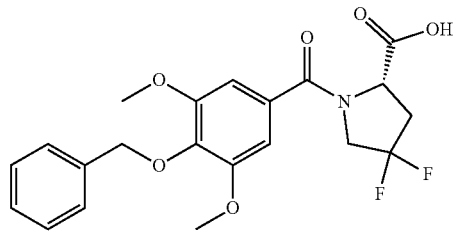 [SMILES: COc1cc(C(=O)N2CC(F)(F)C[C@H]2C(=O)O)cc(OC)c1OCc1ccccc1]

Prepared following Procedure C described above from intermediate 1 (4-benzyloxy-3,5-dimethoxybenzoic acid) (260 mg, 0.9 mmol) and Intermediate 3 ((S)-4,4-difluoropyrrolidine-2-carboxylic acid) (1.0 mmol). Purification by flash chromatography affords the desired product (366 mg, 0.8 mmol).

Intermediate 11: (2S,4S)-1-(4-(benzyloxy)-3,5-dimethoxybenzoyl)-4-(methylthio)-pyrrolidine-2-carboxylic Acid

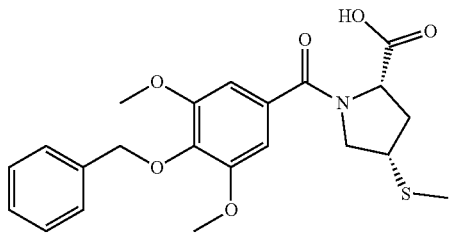 [SMILES: COc1cc(C(=O)N2C[C@@H](SC)C[C@H]2C(=O)O)cc(OC)c1OCc1ccccc1]

Prepared following Procedure C described above from Intermediate 1 (4-benzyloxy-3,5-dimethoxybenzoic acid) (505 mg, 1.75 mmol) and Intermediate 4 ((2S,4S)-4-(methylthio)pyrrolidine-2-carboxylic acid) (1.93 mmol). Purification by flash chromatography affords the desired product (537 mg, 1.24 mmol).

Intermediate 12: (2S,4S)-1-(benzyloxy)-3,5-dimethoxybenzoyl)-4-methylpyrrolidine-2-carboxylic Acid

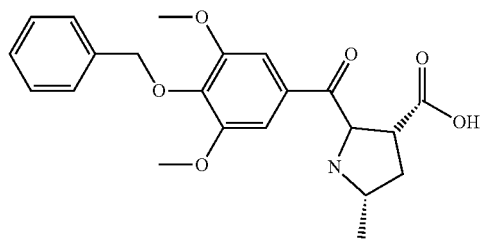

Prepared following Procedure C described above from intermediate 1 (4-benzyloxy-3,5-dimethoxybenzoic acid) (384 mg, 1.33 mmol) and Intermediate 5 ((2S,4S)-4-methylpyrrolidine-2-carboxylic acid) (1.47 mmol). Purification by flash chromatography affords the desired product (342 mg, 0.85 mmol).

Intermediate 13: (2S,4R)-1-(4-(benzyloxy)-3,5-dimethoxybenzoyl)-4-acetoxypyrrolidine-2-carboxylic Acid

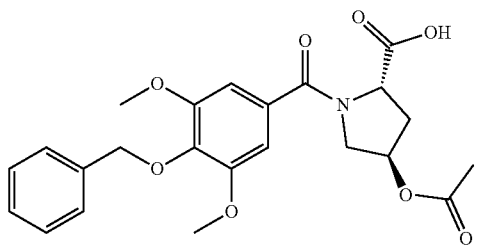 [SMILES: COc1cc(C(=O)N2C[C@H](OC(C)=O)C[C@H]2C(=O)O)cc(OC)c1OCc1ccccc1]

Prepared following Procedure C described above from Intermediate 1 (4-benzyloxy-3,5-dimethoxybenzoic acid) (400 mg, 1.39 mmol) and Intermediate 6 ((2S,4R)-4-acetoxypyrrolidine-2-carboxylic acid) (1.53 mmol). Purification by flash chromatography affords the desired product (342 mg, 0.85 mmol).

Intermediate 14: 4-acetoxy-3,5-dimethoxybenzoic Acid

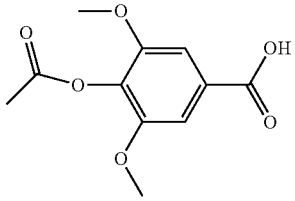 [SMILES: COc1cc(C(=O)O)cc(OC)c1OC(C)=O]

4-Hydroxy-3,5-dimethoxybenzoic acid (300 mg, 1.51 mmol) is dissolved in pyridine (732 µL, 9.08 mmol) at 0° C. Acetic anhydride (214 µL, 2.27 mmol) is added dropwise while the mixture is stirred. The ice bath is kept for 2 h, after which the mixture is poured into ice water. The mixture is extracted with DCM (3×), the organic phase is washed with 1N HCl solution (3×), with water and with brine, dried over sodium sulfate, filtered and evaporated, to give 4-acetoxy-3,5-dimethoxybenzoic acid (286 mg, 1.10 mmol).

Intermediate 15: 4-benzoyloxy-3,5-dimethoxybenzoic Acid

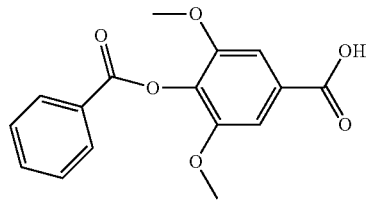 [SMILES: COc1cc(C(=O)O)cc(OC)c1OC(=O)c1ccccc1]

4-Hydroxy-3,5-dimethoxybenzoic acid (300 mg, 1.51 mmol) is dissolved in water (6 mL) and then isopropanol (2.5 mL) is added, followed by potassium carbonate (523 mg, 3.78 mmol). The mixture is kept under argon and cooled to 0° C. Then, benzoyl chloride (185 µL, 1.59 mmol) is added dropwise to the vigorously stirred reaction mixture. A thick white precipitate is formed during the addition. The mixture is stirred for an additional 20 min before being quenched with 6M HCl, while keeping the reaction mixture cool. The solid is collected by filtration, washed with cold water and dried to give 4-benzoyloxy-3,5-dimethoxybenzoic acid as a white solid (401 mg, 1.33 mmol).

Intermediate 16: 3,4-dibenzyloxy-5-methoxybenzoic Acid

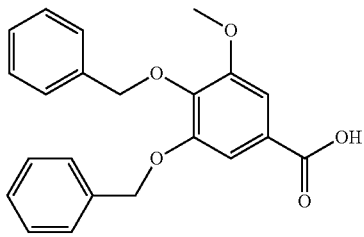 [SMILES: COc1cc(C(=O)O)cc(OCc2ccccc2)c1OCc1ccccc1]

Methyl 3,4-dihydroxy-5-methoxybenzoate (300 mg, 1.51 mmol), potassium carbonate (1.0 g, 7.3 mmol) and potassium iodide (161 mg, 0.97 mmol) are introduced in a round-bottom flask. Acetone (60 mL) is added. The reaction is stirred at room temperature for 30 minutes. Then, benzyl chloride (1.39 mL, 12.1 mmol) is added to the reaction mixture and stirring is maintained at reflux during 8 hours. Afterwards, the reaction is left to cool to room temperature. Water is added and three extractions with diethyl ether are performed, the organic extract is washed with brine, dried and evaporated. The crude product is purified by flash chromatography, yielding 377 mg (1.0 mmol). Subsequently, hydrolysis of the methyl ester is performed following Procedure A described above, to give 3,4-dibenzyloxy-5-methoxybenzoic acid (144 mg, 0.4 mmol).

Intermediate 17: 3,4-dibenzoyloxy-5-methoxybenzoic Acid

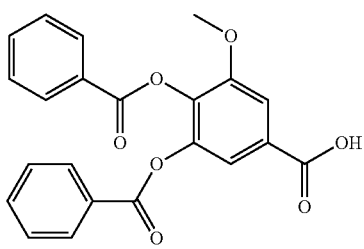 [SMILES: COc1cc(C(=O)O)cc(OC(=O)c2ccccc2)c1OC(=O)c1ccccc1]

3,4-Dihydroxy-5-methoxybenzoic acid (300 mg, 1.63 mmol) is dissolved in water (6 mL) and then Isopropanol (2.5 ml) is added, followed by potassium carbonate (1.13 g, 8.15 mmol). The mixture is kept under argon and cooled to 0° C. Then, benzoyl chloride (388 µL, 3.34 mmol) is added dropwise to the vigorously stirred reaction mixture. The mixture is stirred for an additional 20 min before being quenched with 6M HCl, while keeping the reaction mixture cool. Then, it is diluted with AcOEt and the phases are separated. The organic phase is washed successively with 1M HCl solution and with brine, dried over sodium sulfate, filtered and evaporated. Purification of the crude by flash chromatography gives 3,4-dibenzoyloxy-5-methoxybenzoic acid as a white solid (548 mg, 1.40 mmol).

Intermediate 18: 3-acetoxy-4,5-dimethoxybenzoic Acid

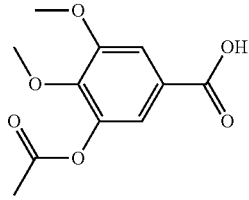 [SMILES: COc1cc(C(=O)O)cc(OC(C)=O)c1OC]

3-Hydroxy-4,5-dimethoxybenzoic acid (300 mg, 1.51 mmol) is dissolved in pyridine (732 µL, 9.08 mmol) at 0° C. Acetic anhydride (214 µL, 2.27 mmol) is added dropwise while the mixture is stirred. The ice bath is kept for 2 h, after which the mixture is poured into ice water. The mixture is extracted with DCM (3×), the organic phase is washed with 1N HCl solution (3×), with water (2×) and with brine (2×), dried over sodium sulfate, filtered and evaporated to give 3-acetoxy-4,5-dimethoxybenzoic acid (277 mg, 1.15 mmol).

Intermediate 19: 3-pivaloyloxy-4,5-dimethoxybenzoic Acid

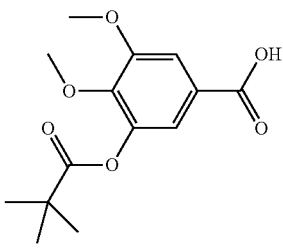 [SMILES: COc1cc(C(=O)O)cc(OC(=O)C(C)(C)C)c1OC]

A solution of 3-hydroxy-4,5-dimethoxybenzoic acid (300 mg, 1.51 mmol) and pyridine (244 µL, 3.02 mmol) in chloroform (2 mL) is stirred for 30 min. To this reaction mixture is added dropwise a solution of pivaloyl chloride (196 µL, 1.59 mmol) in chloroform (2 mL) at room temperature, and the reaction is stirred until its completion according to TLC (around 3 h). Then, the reaction mixture is diluted with DCM, a 1M HCl solution is added and the phases are separated. The organic phase is successively washed with 1M HCl solution (2×), with water and with brine, dried over sodium sulfate, filtered and evaporated. Purification by flash chromatography affords 4-pivaloyloxy-3,5-dimethoxybenzoic acid (321 mg, 1.14 mmol).

Intermediate 20: 4-benzyloxy-3-trifluoromethylbenzoic Acid

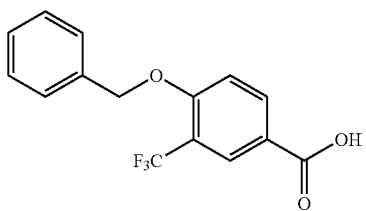 [SMILES: O=C(O)c1ccc(OCc2ccccc2)c(C(F)(F)F)c1]

4-hydroxy-3-trifluoromethylbenzoic acid (1.0 g, 4.9 mmol) and potassium carbonate (1.6 g, 11.6 mmol) are introduced in a round-bottom flask. DMF (10 mL) is added and the reaction is stirred at room temperature for 5 minutes. Then, benzyl chloride (2.2 mL, 19.4 mmol) is added to the reaction mixture is maintained at reflux during 4 hours. Afterwards, the reaction is left to cool to room temperature. Water is added and three extractions with ethyl acetate (3×50 mL) are performed, the organic extract is washed with brine, dried and evaporated. The crude product is purified by flash chromatography, yielding 1.3 g (3.4 mmol). Subsequently, hydrolysis of the benzyl ester is performed following Procedure A described above, to give 4-benzyloxy-3-trifluoromethylbenzoic acid (320 mg, 1.1 mmol).

Intermediate 21: 4-benzyloxy-3-fluorobenzoic Acid

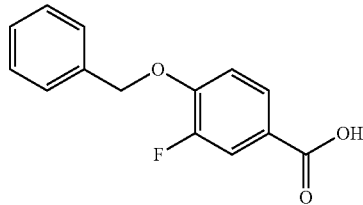 [SMILES: O=C(O)c1ccc(OCc2ccccc2)c(F)c1]

4-hydroxy-3-fluorobenzoic acid (1.0 g, 6.4 mmol), potassium carbonate (2.7 g, 19.2 mmol) and potassium iodide (532 mg, 3.2 mmol) are introduced in a round-bottom flask. Acetone (140 mL) is added and the reaction is stirred at room temperature for 30 minutes. Then, benzyl bromide (3.8 mL, 32.0 mmol) is added to the reaction mixture is maintained at reflux during 12 hours. Afterwards, the reaction is left to cool to room temperature. Water is added and three extractions with ethyl acetate (3×50 mL) are performed, the organic extract is washed with brine, dried and evaporated. The crude product is purified by flash chromatography, yielding 1.2 g (3.5 mmol). Subsequently, hydrolysis of the benzyl ester is performed following Procedure A described above, to give 4-benzyloxy-3-fluoromethylbenzoic acid (612 mg, 2.5 mmol).

Example 1

(S)-1-((2S,4R)-1-(4-(benzyloxy)-3,5-dimethoxybenzoyl)-4-methoxypyrrolidine-2-carbonyl)pyrrolidine-2-carbonitrile

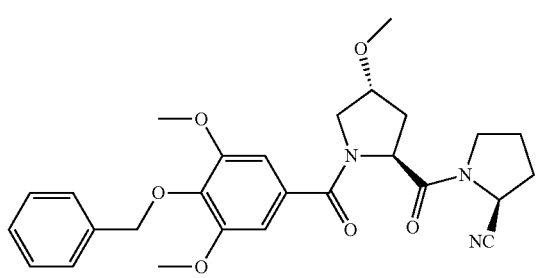 [SMILES: COc1cc(C(=O)N2C[C@H](OC)C[C@H]2C(=O)N2CCC[C@H]2C#N)cc(OC)c1OCc1ccccc1]

Commercially available (S)-pyrrolidine-2-carbonitrile (58 mg, 0.4 mmol) and Intermediate 7 ((2S,4R)-1-(4-(benzyloxy)-3,5-dimethoxybenzoyl)-4-methoxypyrrolidine-2-carboxylic acid) (220 mg, 0.5 mmol) are coupled following Procedure D described above. Purification by RP-HPLC affords 10 mg (0.02 mmol) of final product.

Example 2

(S)-1-((2S,4R)-1-(4-(benzyloxy)-3,5-dimethoxybenzoyl)-4-fluoropyrrolidine-2-carbonyl)pyrrolidine-2-carbonitrile

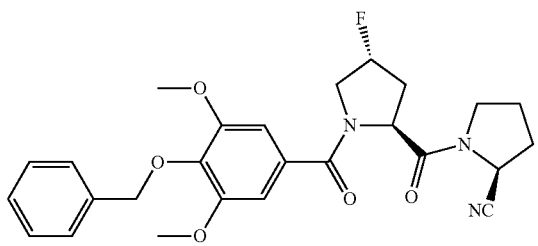 [SMILES: COc1cc(C(=O)N2C[C@H](F)C[C@H]2C(=O)N2CCC[C@H]2C#N)cc(OC)c1OCc1ccccc1]

Starting from commercially available Sieber amide resin (500 mg, 0.30 mmol, 1 eq), commercially available Fmoc-protected L-Proline (Fmoc-L-Pro-OH) (400 mg, 1.2 mmol) and Intermediate 8 ((2S,4R)-1-(4-(benzyloxy)-3,5-dimethoxybenzoyl)-4-fluoropyrrolidine-2-carboxylic acid) (239 mg, 0.60 mmol), the product is prepared following Procedure E described above. Purification by RP-HPLC affords 80 mg (0.17 mmol) of final product.

Example 3

(S)-1-((2S,4S)-1-(4-(benzyloxy)-3,5-dimethoxybenzoyl)-4-phenylpyrrolidine-2-carbonyl)pyrrolidine-2-carbonitrile

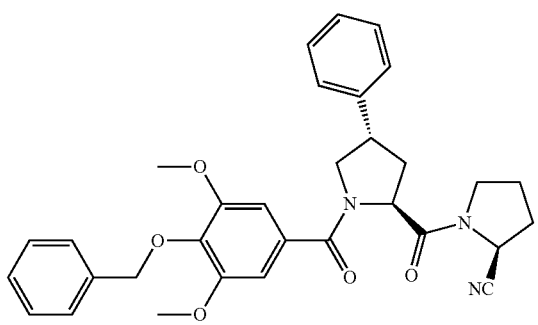 [SMILES: COc1cc(C(=O)N2C[C@H](c3ccccc3)C[C@H]2C(=O)N2CCC[C@H]2C#N)cc(OC)c1OCc1ccccc1]

Starting from commercially available Sieber amide resin (500 mg, 0.38 mmol, 1 eq), commercially available Fmoc-protected L-Proline (Fmoc-L-Pro-OH) (516 mg, 1.53 mmol) and Intermediate 9 ((2S,4S)-1-(4-(benzyloxy)-3,5-dimethoxybenzoyl)-4-phenylpyrrolidine-2-carboxylic acid) (351 mg, 0.76 mmol), the product is prepared following Procedure E described above. Purification by RP-HPLC affords 16 mg (0.03 mmol) of final product.

Example 4

(S)-1-((2S)-1-(4-(benzyloxy)-3,5-dimethoxybenzoyl)-4,4-difluoropyrrolidine-2-carbonyl)pyrrolidine-2-carbonitrile

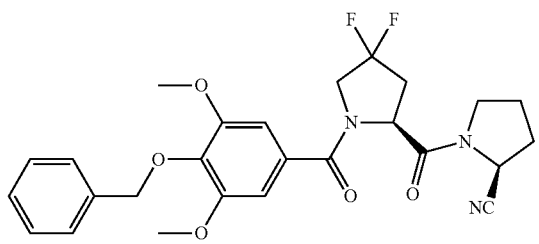 [SMILES: COc1cc(C(=O)N2CC(F)(F)C[C@H]2C(=O)N2CCC[C@H]2C#N)cc(OC)c1OCc1ccccc1]

Starting from commercially available Sieber amide resin (250 mg, 0.19 mmol, 1 eq), commercially available Fmoc-protected L-Proline (Fmoc-L-Pro-OH) (258 mg, 0.77 mmol) and Intermediate 10 ((S)-1-(4-(benzyloxy)-3,5-dimethoxybenzoyl)-4,4-difluoropyrrolidine-2-carboxylic acid) (161 mg, 0.38 mmol), the product is prepared following Procedure E described above. Purification by RP-HPLC affords 18 mg (0.036 mmol) of final product.

Example 5

(S)-1-((2S,4S)-1-(4-(benzyloxy)-3,5-dimethoxybenzoyl)-4-(methylthio)pyrrolidine-2-carbonyl)pyrrolidine-2-carbonitrile

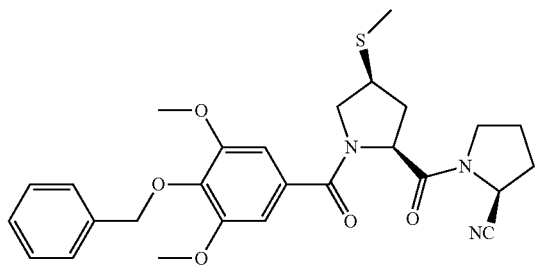 [SMILES: COc1cc(C(=O)N2C[C@@H](SC)C[C@H]2C(=O)N2CCC[C@H]2C#N)cc(OC)c1OCc1ccccc1]

Starting from commercially available Sieber amide resin (500 mg, 0.38 mmol, 1 eq), commercially available Fmoc-protected L-Proline (Fmoc-L-Pro-OH) (516 mg, 1.53 mmol) and Intermediate 11 ((2S,4S)-1-(4-(benzyloxy)-3,5-dimethoxybenzoyl)-4-(methylthio)pyrrolidine-2-carboxylic acid) (330 mg, 0.76 mmol), the product is prepared following Procedure E described above. Purification by RP-HPLC affords 22 mg (0.043 mmol) of final product.

Example 6

(S)-1-((2S,4S)-1-(4-(benzyloxy)-3,5-dimethoxybenzoyl)-4-methylpyrrolidine-2-carbonyl)pyrrolidine-2-carbonitrile

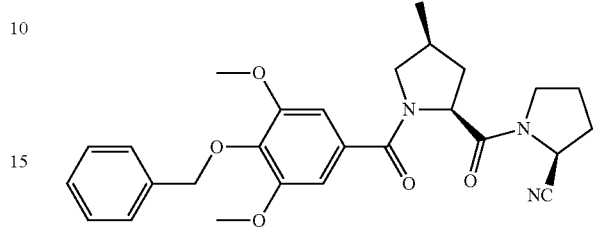

Starting from commercially available Sieber amide resin (300 mg, 0.18 mmol, 1 eq), commercially available Fmoc-protected L-Proline (Fmoc-L-Pro-OH) (247 mg, 0.73 mmol) and Intermediate 12 ((2S,4S)-1-(4-(benzyloxy)-3,5-dimethoxybenzoyl)-4-methylpyrrolidine-2-carboxylic acid) (146 mg, 0.37 mmol), the product is prepared following Procedure E described above. Purification by RP-HPLC affords 10 mg (0.02 mmol) of final product.

Example 7

(S)-1-((2S,4R)-1-(4-(benzyloxy)-3,5-dimethoxybenzoyl)-4-cyanopyrrolidine-2-carbonyl)pyrrolidine-2-carbonitrile

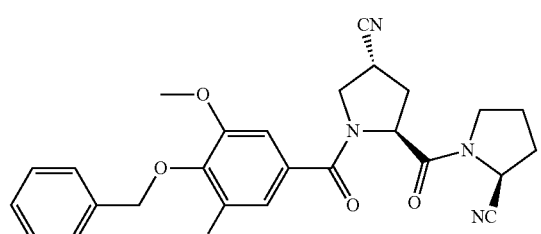

Commercially available Fmoc-protected L-Proline (Fmoc-L-Pro-OH) (516 mg, 1.53 mmol) and Boc-trans-4-cyano-L-proline (368 mg, 1.53 mmol) are sequentially coupled onto commercially available Sieber amide resin (500 mg, 0.38 mmol, 1 eq), through stepwise coupling as described in Procedure E above. After cleavage of the dipeptide from the resin, intermediate 1 (4-benzyloxy-3,5-dimethoxybenzoic acid) (145 mg, 0.5 mmol) is coupled to the resulting nitrile dipeptide following Procedure C, via formation of the carboxylic acid chloride. Purification of the crude by RP-HPLC affords 11 mg (0.03 mmol) of final product.

Example 8

(S)-1-((2S,4S)-1-(4-(benzyloxy)-3,5-dimethoxybenzoyl)-4-(trifluoromethyl)-pyrrolidine-2-carbonyl)pyrrolidine-2-carbonitrile

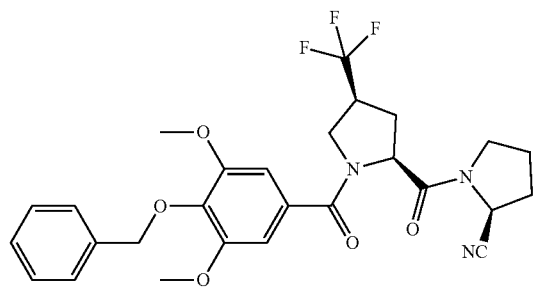 [SMILES: COc1cc(C(=O)N2C[C@@H](C(F)(F)F)C[C@H]2C(=O)N2CCC[C@H]2C#N)cc(OC)c1OCc1ccccc1]

Commercially available Fmoc-protected L-Proline (Fmoc-L-Proline-OH) (135 mg, 0.40 mmol), (2S,4S)-Fmoc-4-trifluoromethyl-pyrrolidine-2-carboxylic acid (162 mg, 0.40 mmol), and Intermediate 1 (4-benzyloxy-3,5-dimethoxybenzoic acid) (115 mg, 0.40 mmol) are sequentially coupled onto commercially available Sieber amide resin (165 mg, 0.10 mmol, 1 eq), through stepwise coupling as described in Procedure E above. Purification by RP-HPLC affords 13 mg (0.045 mmol) of final product.

Example 9

(S)-1-((2S,4R)-1-(4-(benzyloxy)-3,5-dimethoxybenzoyl)-4-(tert-butoxy) pyrrolidine-2-carbonyl)pyrrolidine-2-carbonitrile

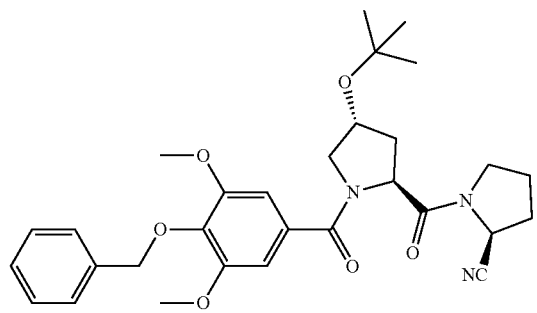 [SMILES: COc1cc(C(=O)N2C[C@H](OC(C)(C)C)C[C@H]2C(=O)N2CCC[C@H]2C#N)cc(OC)c1OCc1ccccc1]

Commercially available Fmoc-protected L-Proline (Fmoc-L-Pro-OH) (135 mg, 0.40 mmol), Fmoc-4-tert-butoxy-L-proline (164 mg, 0.40 mmol), and Intermediate 1 (4-benzyloxy-3,5-dimethoxybenzoic acid) (115 mg, 0.40 mmol) are sequentially coupled onto commercially available Sieber amide resin (165 mg, 0.10 mmol, 1 eq), through stepwise coupling as described in Procedure E above. Purification by RP-HPLG affords 22 mg (0.076 mmol) of final product.

Example 10

(S)-1-((2S,4R)-1-(4-(benzyloxy)-3,5-dimethoxybenzoyl)-4-acetoxypyrrolidine-2-carbonyl)pyrrolidine-2-carbonitrile

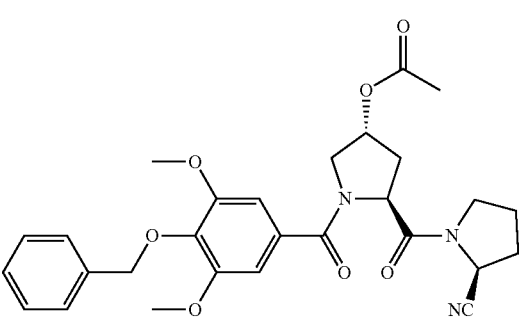 [SMILES: COc1cc(C(=O)N2C[C@H](OC(C)=O)C[C@H]2C(=O)N2CCC[C@H]2C#N)cc(OC)c1OCc1ccccc1]

Starting from commercially available Sieber amide resin (165 mg, 0.10 mmol, 1 eq), commercially available Fmoc-protected L-Proline (Fmoc-L-Pro-OH) (135 mg, 0.40 mmol) and intermediate 13 ((2S,4R)-1-(4-(benzyloxy)-3,5-dimethoxybenzoyl)-4-acetoxypyrrolidine-2-carboxylic acid) (90 mg, 0.20 mmol), the product is prepared following Procedure E described above. Purification by RP-HPLC affords 6.2 mg (0.012 mmol) of final product.

Example 11

(S)-1-((2S)-1-(4-acetoxy-3,5-dimethoxybenzoyl)-4,4-difluoropyrrolidine-2-carbonyl)pyrrolidine-2-carbonitrile

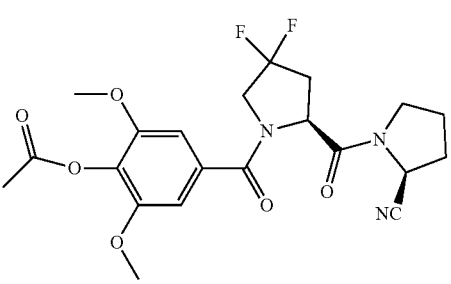 [SMILES: COc1cc(C(=O)N2CC(F)(F)C[C@H]2C(=O)N2CCC[C@H]2C#N)cc(OC)c1OC(C)=O]

Commercially available Fmoc-protected L-Proline (Fmoc-L-Pro-OH) (135 mg, 0.40 mmol), Fmoc-4,4-difluoro-L-proline (149 mg, 0.40 mmol) and Intermediate 14 (4-acetoxy-3,5-dimethoxybenzoic acid) (96 mg, 0.40 mmol) are sequentially coupled onto commercially available Sieber amide resin (165 mg, 0.10 mmol, 1 eq), through stepwise coupling as described in Procedure E above. Purification by RP-HPLC affords 25 mg (0.054 mmol) of final product.

Example 12

(S)-1-((2S)-1-(4-benzoyloxy-3,5-dimethoxybenzoyl)-4,4-difluoropyrrolidine-2-carbonyl)pyrrolidine-2-carbonitrile

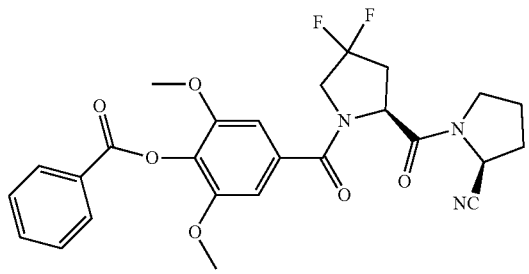 [SMILES: COc1cc(C(=O)N2CC(F)(F)C[C@H]2C(=O)N2CCC[C@H]2C#N)cc(OC)c1OC(=O)c1ccccc1]

Commercially available Fmoc-protected L-Proline (Fmoc-L-Pro-OH) (135 mg, 0.4 mmol), Fmoc-4,4-difluoro-L-proline (149 mg, 0.4 mmol) and Intermediate 15 (4-benzoyloxy-3,5-dimethoxybenzoic acid) (121 mg, 0.4 mmol) are sequentially coupled onto commercially available Sieber amide resin (165 mg, 0.1 mmol, 1 eq), through stepwise coupling as described in Procedure E above. Purification by RP-HPLC affords 26 mg (0.051 mmol) of final product.

Example 13

(S)-1-((2S)-1-(3,4-dibenzyloxy-5-methoxybenzoyl)-4,4-difluoropyrrolidine-2-carbonyl)pyrrolidine-2-carbonitrile

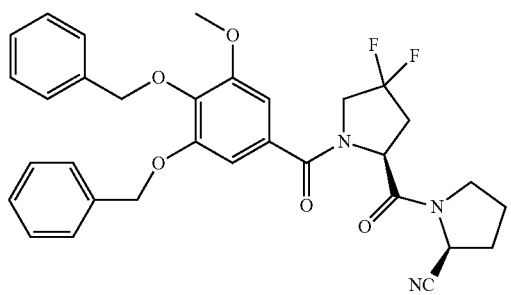 [SMILES: COc1cc(C(=O)N2CC(F)(F)C[C@H]2C(=O)N2CCC[C@H]2C#N)cc(OCc2ccccc2)c1OCc1ccccc1]

Commercially available Fmoc-protected L-Proline (Fmoc-L-Pro-OH) (135 mg, 0.4 mmol), Fmoc-4,4-difluoro-L-proline (149 mg, 0.4 mmol) and intermediate 16 (3,4-dibenzyloxy-5-methoxybenzoic acid) (146 mg, 0.4 mmol) are sequentially coupled onto commercially available Sieber amide resin (165 mg, 0.1 mmol, 1 eq), through stepwise coupling as described in Procedure E above. Purification by RP-HPLC affords 24 mg (0.041 mmol) of final product.

Example 14

(S)-1-((2S)-1-(3,4-dibenzoyloxy-5-methoxybenzoyl)-4,4-difluoropyrrolidine-2-carbonyl)pyrrolidine-2-carbonitrile

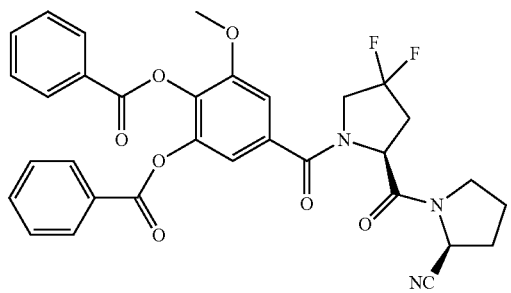 [SMILES: COc1cc(C(=O)N2CC(F)(F)C[C@H]2C(=O)N2CCC[C@H]2C#N)cc(OC(=O)c2ccccc2)c1OC(=O)c1ccccc1]

Commercially available Fmoc-protected L-Proline (Fmoc-L-Pro-OH) (135 mg, 0.4 mmol), Fmoc-4,4-difluoro-L-proline (149 mg, 0.4 mmol) and Intermediate 17 (3,4-dibenzoyloxy-5-methoxybenzoic acid) (157 mg, 0.4 mmol) are sequentially coupled onto commercially available Sieber amide resin (165 mg, 0.1 mmol, 1 eq), through stepwise coupling as described in Procedure E above. Purification by RP-HPLC affords 31 mg (0.052 mmol) of final product.

Example 15

(S)-1-((2S)-1-(3-acetoxy-4,5-dimethoxybenzoyl)-4,4-difluoropyrrolidine-2-carbonyl)pyrrolidine-2-carbonitrile

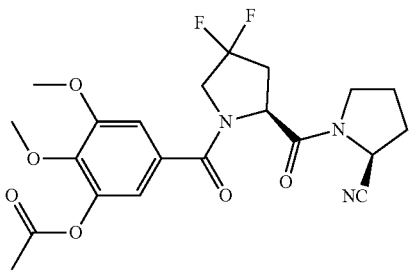 [SMILES: COc1cc(C(=O)N2CC(F)(F)C[C@H]2C(=O)N2CCC[C@H]2C#N)cc(OC(C)=O)c1OC]

Commercially available Fmoc-protected L-Proline (Fmoc-L-Pro-OH) (135 mg, 0.4 mmol), Fmoc-4,4-difluoro-L-proline (149 mg, 0.4 mmol) and Intermediate 18 (3-acetoxy-4,5-dimethoxybenzoic acid) (96 mg, 0.4 mmol) are sequentially coupled onto commercially available Sieber amide resin (165 mg, 0.1 mmol, 1 eq), through stepwise coupling as described in Procedure E above. Purification by RP-HPLC affords 22 mg (0.048 mmol) of final product.

Example 16

(S)-1-((2S)-1-(3-pivaloyloxy-4,5-dimethoxybenzoyl)-4,4-difluoropyrrolidine-2-carbonyl)pyrrolidine-2-carbonitrile

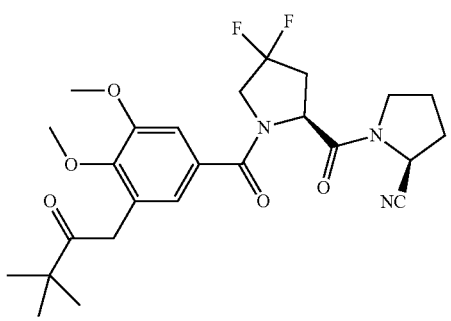 [SMILES: COc1cc(C(=O)N2CC(F)(F)C[C@H]2C(=O)N2CCC[C@H]2C#N)cc(CC(=O)C(C)(C)C)c1OC]

Commercially available Fmoc-protected L-Proline (Fmoc-L-Pro-OH) (135 mg, 0.4 mmol), Fmoc-4,4-difluoro-L-proline (149 mg, 0.4 mmol) and Intermediate 19 (3-pivaloyloxy-4,5-dimethoxybenzoic acid) (113 mg, 0.4 mmol) are sequentially coupled onto commercially available Sieber amide resin (165 mg, 0.1 mmol, 1 eq), through stepwise coupling as described in Procedure E above. Purification by RP-HPLC affords 19 mg (0.040 mmol) of final product.

Example 17

(S)-1-((S)-1-(4-(benzyloxy)benzoyl)-4,4-difluoropyrrolidine-2-carbonyl)pyrrolidine-2-carbonitrile

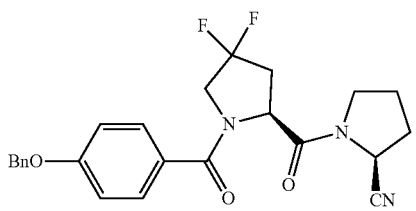 [SMILES: N#C[C@@H]1CCCN1C(=O)[C@@H]1CC(F)(F)CN1C(=O)c1ccc(OCc2ccccc2)cc1]

Commercially available Fmoc-protected L-Proline (Fmoc-L-Pro-OH) (150 mg, 0.45 mmol), Fmoc-4,4-difluoro-L-proline (166 mg, 0.45 mmol) and 4-benzyloxybenzoic acid (101 mg, 0.45 mmol) are sequentially coupled onto commercially available Sieber amide resin (200 mg, 0.15 mmol, 1 eq), through stepwise coupling as described in Procedure E above. Purification by RP-HPLC affords 17 mg (0.038 mmol) of final product.

Example 18

(S)-1-((S)-1-(3-(benzyloxy)benzoyl)-4,4-difluoropyrrolidine-2-carbonyl)pyrrolidine-2-carbonitrile

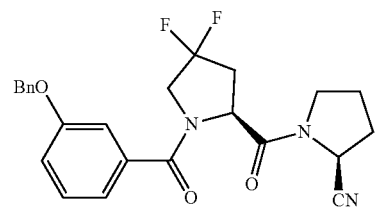 [SMILES: N#C[C@@H]1CCCN1C(=O)[C@@H]1CC(F)(F)CN1C(=O)c1cccc(OCc2ccccc2)c1]

Commercially available Fmoc-protected L-Proline (Fmoc-L-Pro-OH) (150 mg, 0.45 mmol), Fmoc-4,4-difluoro-L-proline (166 mg, 0.45 mmol) and 3-benzyloxybenzoic acid (101 mg, 0.45 mmol) are sequentially coupled onto commercially available Sieber amide resin (200 mg, 0.15 mmol, 1 eq), through stepwise coupling as described in Procedure E above. Purification by RP-HPLC affords 8 mg (0.018 mmol) of final product.

Example 19

(S)-1-((S)-1-(2-(benzyloxy)benzoyl)-4,4-difluoropyrrolidine-2-carbonyl)pyrrolidine-2-carbonitrile

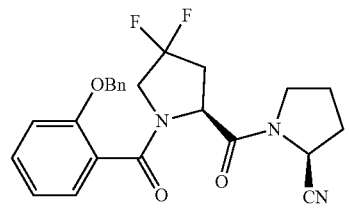 [SMILES: N#C[C@@H]1CCCN1C(=O)[C@@H]1CC(F)(F)CN1C(=O)c1ccccc1OCc1ccccc1]

Commercially available Fmoc-protected L-Proline (Fmoc-L-Pro-OH) (150 mg, 0.45 mmol), Fmoc-4,4-difluoro-L-proline (166 mg, 0.45 mmol) and 2-benzyloxybenzoic acid (101 mg, 0.45 mmol) are sequentially coupled onto commercially available Sieber amide resin (200 mg, 0.15 mmol, 1 eq), through stepwise coupling as described in Procedure E above. Purification by RP-HPLC affords 5 mg (0.011 mmol) of final product.

Example 20

(S)-1-((S)-1-(4-(benzyloxy)-3-(trifluoromethyl)benzoyl)-4,4-difluoropyrrolidine-2-carbonyl)pyrrolidine-2-carbonitrile

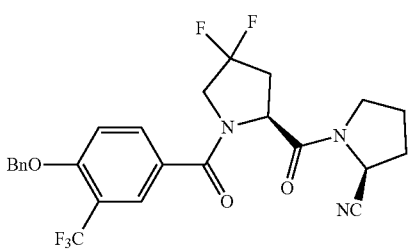 [SMILES: N#C[C@@H]1CCCN1C(=O)[C@@H]1CC(F)(F)CN1C(=O)c1ccc(OCc2ccccc2)c(C(F)(F)F)c1]

Commercially available Fmoc-protected L-Proline (Fmoc-L-Pro-OH) (150 mg, 0.45 mmol), Fmoc-4,4-difluoro-L-proline (186 mg, 0.45 mmol) and Intermediate 20 (4-benzyloxy-3-trifluoromethylbenzoic acid) (132 mg, 0.45 mmol) are sequentially coupled onto commercially available Sieber amide resin (200 mg, 0.15 mmol, 1 eq), through stepwise coupling as described in Procedure E above. Purification by RP-HPLC affords 32 mg (0.061 mmol) of final product.

Example 21

(S)-1-((S)-1-(4-(benzyloxy)-3-fluorobenzoyl)-4,4-difluoropyrrolidine-2-carbonyl)pyrrolidine-2-carbonitrile

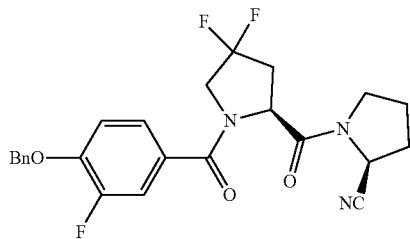 [SMILES: N#C[C@@H]1CCCN1C(=O)[C@@H]1CC(F)(F)CN1C(=O)c1ccc(OCc2ccccc2)c(F)c1]

Commercially available Fmoc-protected L-Proline (Fmoc-L-Pro-OH) (150 mg, 0.45 mmol), Fmoc-4,4-difluoro-L-proline (166 mg, 0.45 mmol) and Intermediate 21 (4-benzyloxy-3-fluorobenzoic acid) (109 mg, 0.45 mmol) are sequentially coupled onto commercially available Sieber amide resin (200 mg, 0.15 mmol, 1 eq), through stepwise coupling as described in Procedure E above. Purification by RP-HPLC affords 14 mg (0.030 mmol) of final product.

Pharmacological Data

Determination of Inhibitory Effect of Novel Compounds on (Human) Prolyl Oligopeptidase Activity Expression and Purification of Prolyl Oligopeptidase (POP)

POP was obtained by expression in E. coli and affinity purification using a His tail fusion according to a literature procedure (Tarragó T et al., ChemBioChem 2006; 7:827-33) summarized below:

hPOP expression: E. coli BL21 competent cells were transformed with pETM10 hPOP. To induce expression, a pre-culture of LB medium (50 mL) containing kanamycin (50 µg/mL) was inoculated with one colony and was grown overnight at 37° C., Next day, two cultures of LB medium (500 ml) were inoculated with the overnight culture (10 mL). The inoculated cultures were grown at 37° C. and 220 rpm until the $OD_{595}$ was 1.2 (2.5-3 hours). IPTG was then added (final concentration of 1 mM) and induction was performed overnight at 25° C., Cells were harvested (3500 g, 15 min, 4° C.) and the pellet was suspended in suspension buffer (50 mL) [Tris-HCl pH 8 (50 mM), NaCl (300 mM), imidazole (1 mM)] and sonicated with use of four cycles (each consisting of 15 sec of sonication and 15 sec of rest) at an intensity of 50% and 0.5 pulses, the sample being kept on ice. After sonication, the sample was centrifuged (40 000 g, 30 min, 4° C.) and the supernatant was used immediately for POP purification. An AKTA explorer FPLC system was used for purification. The supernatant was applied at a flow of 1 mL/min to a HiTrapQuelating column (5 mL) previously equilibrated with 5 column volumes of suspension buffer. The column was washed with suspension buffer until the absorbance at 280 nm returned to basal level. The column was then rinsed with 5 volumes of washing buffer (50 mM Tris-HCl, pH 8, 300 mM NaCl, 30 mM imidazole). The elution was performed with 4 volumes of elution buffer (50 mM Tris-HCl, pH 8, 300 mM NaCl, 500 mM imidazole). Fractions (4 mL) were collected during the entire elution. POP activity was checked in all fractions and positive ones were analyzed by SDS-PAGE and stained with Biosafe Comassie Stain G-250. Positive fractions were collected and desalted by use of a HiPrep 26/10 Desalting column with Tris-HCl (50 mM, pH 8) as buffer. Recombinant hPOP was quantified with the Bio-Rad Protein Assay with BSA as standard, Aliquots of the recombinant enzyme were prepared and immediately frozen with liquid nitrogen and stored at −80° C.

POP Inhibition Assays

POP activity was determined following the method described by Toide et al (Toide K et al., J. Pharmacol. Exp. Ther. 1995; 274:1370-8), using Z-G-P-AMC (N-benzyloxycarbonyl-Gly-Pro-methylcoumarinyl-7-amide) as POP substrate. The reactions were performed in 96-well microtiter plates, which allowed simultaneous monitoring of multiple reactions. For each reaction, activity buffer (134 µl, 100 mM Na/K phosphate buffer, pH 8.0) was pre-incubated for 15 min at 37° C. with hPOP (ranging from 20 to 60 nM, depending on the activity of the hPOP batch) and the corresponding new compound solution (3 µl). A stock solution of new compound was prepared in DMSO (100 mM), and dilutions were prepared from this stock solution with DMSO. Alternatively, the reactions were performed using another activity buffer (141 µL, 100 mM Tris-acetate, 10 mM BSA, 1 mM DTT, pH 7.3), pre-incubating with hPOP (10 nM) and the corresponding new compound solution (3 µl) (Conditions B).

After preincubation, Z-G-P-AMC (10 µl, 3 mM in 40% 1,4-dioxane) was added (3 µL 1.5 mM in 40% of 1,4-dioxane, in Conditions B), and the reaction was incubated for 1 hour at 37° C. The reaction was stopped by adding sodium acetate (150 µl, 1 M, pH 4) and the formation of AMC was measured fluorimetrically. The excitation and emission wavelengths were 360/40 and 485/20 nm, respectively.

Several concentration points (ranging from 25 pM to 400 µM) were measured for each compound. The inhibitory activity on prolyl oligopeptidase was calculated according to eq 1. For each new compound, the fluorescence in the presence (a) and in the absence of hPOP (b) was measured. The maximum fluorescence (0% inhibitory activity) was obtained from a sample of hPOP in the absence of inhibitory compounds. To estimate the inhibitory potency of the novel compound, activities were plotted against the log concentration of the compound, adjusting to a sigmoid curve using GraphPad Prism software, and the $IC_{50}$ value, defined as the concentration of compound required to inhibit 50% of POP activity, was determined from the resulting curve.

$$\text{Inhibitory activity (\%)} = \left[1 - \left(\frac{a-b}{c-d}\right)\right] \times 100 \quad \text{(Equation 1)}$$

wherein:

a corresponds to fluorescence intensity in the presence of substrate+tested compound+hPOP b corresponds to the fluorescence intensity in the presence of substrate+tested compound c corresponds to the fluorescence intensity in the presence of substrate+hPOP d corresponds to the fluorescence intensity of the presence of substrate.

The new compounds exhibit high inhibition potency against human prolyl oligopeptidase. The results are summarized in Table 1.

TABLE 1

Inhibition of human prolyl oligopeptidase.

| Compound (Example n°) | IC$_{50}$ (nM) | SD |
|---|---|---|
| 1 | 63.8 | 11.4 |
| 2 | 60.4 | 10.6 |
| 3 | 339.0 | 138.5 |
| 4 | 48.7 | 20.3 |
| 5 | 175.9 | 72.0 |
| 6 | 13.1 (*) | 7.3 |
| 8 | 176.5 | 8.3 |
| 9 | 668.1 | 327.3 |
| 11 | 352 | — |
| 12 | 111 | — |
| 13 | 336 | — |
| 15 | 5600 | — |
| 16 | 2140 | — |
| 17 | 287.3 (*) | 135.8 |
| 18 | 487.3 (*) | 16.8 |
| 19 | 255.4 (*) | 34.2 |
| 20 | 4.5 (*) | 0.02 |
| 21 | 5.0 (*) | 1.6 |

(*) Measured in conditions B

Inhibitory Activity Against Related Proline Specific Proteases

The inhibitory effect of the new compounds on the activity of dipeptidyl peptidase IV (DPPIV) was tested. The above described procedure for determining the inhibitory activity on prolyl oligopeptidase was followed, using G-P-AMC (H-Gly-Pro-methylcoumarinyl-7-amide) as substrate. After preincubation of DPPIV with the activity buffer and the corresponding compound solution, G-P-AMC (10 μl, 750 μM in 40% 1,4-dioxane) was added, and the reaction was incubated for 20 min at 37° C. The reaction was stopped by adding sodium acetate (150 μl, 1 M, pH 4) and the formation of AMC was measured fluorimetrically. Several concentration points (ranging from 100 μM to 400 μM) were measured for each compound. The Inhibitory activity on DPPIV was calculated according to eq 1. None of the novel compounds showed inhibitory activity against dipeptidyl peptidase IV (IC$_{50}$ values over 400 μM), and are therefore specific POP inhibitors.

Additionally, the inhibitory activity of the new compounds against fibroblast activation protein (FAR) was tested. A procedure similar to the one described above for the determination of the inhibitory activity on POP was followed. Z-G-P-AMC was used as a substrate, at a final concentration of 100 μM. The buffer used in the assays was 50 mM Tris, 1M NaCl, 1 mg/ml BSA pH: 7.5. Recombinant human FAP was used at a stock concentration of 2 μg/mL in activity buffer, leading to a final concentration 0.1 μg/mL in the assay. Stock solutions of the each new compound were prepared at 20 mM in DMSO and diluted conveniently. After preincubation of FAP with the activity buffer and the corresponding new compound solution at 37° C. for 15 min, the substrate (50 μl, 100 μM in activity buffer) was added, and the reaction was incubated for 1 h at 37° C. The reaction was stopped by adding sodium acetate (150 μl, 1 M, pH 4) and the formation of AMC was measured fluorimetrically. Several concentration points (ranging from 100 μM to 400 μM) were measured for each compound. The inhibitory activity on FAP was calculated according to eq 1. None of the novel compounds showed inhibitory activity against FAP (IC$_{50}$ values over 400 μM), and are therefore specific POP inhibitors.

Determination of Permeability Properties of the Compounds

Parallel Artificial Membrane Permeability Assay (PAMPA)

Parallel artificial membrane permeability assay (PAMPA) described in Kansy M et al., *J. Med. Chem.* 1998; 47(7): 1007-10 was used to determine the capacity of compounds to cross the Blood-Brain Barrier (BBB) by passive diffusion (Di L et al., *Eur. J. Med. Chem.* 2003; 38(3):223-32). The effective permeability ($P_e$) of the compounds was measured at an initial concentration of 200 μM. The buffer solution was prepared from a commercial concentrated one following the manufacturer's instructions. pH was adjusted to 7.4 using a 0.5 M NaOH solution. A stock solution of new compound was prepared in DMSO and diluted with buffer solution to a final 200 μM concentration (0.5% DMSO content). The PAMPA sandwich was separated and each donor well was filled with 200 μL of the compound solution. The acceptor plate was placed into the donor plate, ensuring that the underside of the membrane was in contact with buffer. 4 μL of the mixture of phospholipids (20 mg/mL) in dodecane was added to the filter of each well, and 200 μL of buffer solution was added to the each acceptor well. The plate was covered and incubated at room temperature in a saturated humidity atmosphere for 4 hours under orbital agitation at 100 rpm. After 4 hours, the contents of the acceptor and donor compartments were analyzed by HPLC: 150 μL of each well from the donor plate and 150 μL of each well from the acceptor plate were transferred to HPLC vials, injecting each sample into a reverse-phase C$_{18}$ column (150 mm×4.6 mm×5 μm, 100 Å) (100 μL/injection from the acceptor wells, 10 μL/injection from the donor wells and for t$_0$ references). Transport was also confirmed by MALDI-TOF spectrometry.

The phospholipid mixture used was a porcine polar brain lipid extract, provided by Avanti polar lipids, with the following composition: 12.6% phosphatidylcholine (PC), 33.1% phosphatidylethanolamine (PE), 18.5% phosphatidyiserine (PS), 4.1% phosphatidylinositol (PI), 0.8% phosphatide acid and 30.9% of other compounds.

The effective permeability ($P_e$) after 4 hours was calculated using equation 2 and the percentage of transport was calculated using equation 3:

$$P_e = \frac{-218.3}{t} \times \log\left[1 - \frac{2C_A(t)}{C_D(t_0)}\right] \times 10^{-6} \text{ cm/s} \quad \text{(Equation 2)}$$

$$T\% = \frac{C_A(t)}{C_D(t_0)} \times 100 \quad \text{(Equation 3)}$$

wherein:

t is time (h)

$C_A(t)$ is the compound concentration in the acceptor well at time t and $C_D(t_0)$ is the compound concentration in the donor well at $t_0$.

Based on the indicative Pe values shown in Table 2, the novel compounds show good permeability across the BBB (Table 3)

TABLE 2

Indicative $P_e$ values

| Indicative $P_e$ values (cm/s) | Transport inside CNS |
|---|---|
| $P_e >= 4 \cdot 10^{-6}$ | Good |
| $2 \cdot 10^{-6} <= P_e < 4 \cdot 10^{-6}$ | Questionable |
| $P_e < 2 \cdot 10^{-6}$ | Bad |

TABLE 3

Effective permeability ($P_e$) and percentage of transport of the new compounds

| Compound (Example N°) | Pe (×10⁻⁶ cm/s) | SD | % T | SD |
|---|---|---|---|---|
| 1 | 1.00 | 0.1 | 4.3 | — |
| 2 | 7.28 | 2.75 | 13.03 | 4.39 |
| 3 | 2.89 | 0.84 | 5.72 | 1.58 |
| 4 | 22.14 | 5.86 | 29.92 | 4.80 |
| 5 | 9.98 | 3.07 | 17.03 | 4.25 |
| 6 | 3.79 | 0.16 | 14.76 | 0.59 |
| 8 | 5.07 | 0.30 | 19.27 | 1.00 |
| 12 | 2.10 | 0.02 | 8.47 | 0.06 |
| 16 | 5.02 | 0.30 | 19.08 | 1.01 |
| 17 | 8.04 | 3.13 | 14.12 | 4.69 |
| 18 | 6.51 | 1.79 | 11.91 | 2.88 |
| 19 | 10.29 | 1.50 | 17.55 | 2.03 |
| 20 | 1.29 | 0.66 | 2.64 | 1.33 |
| 21 | 5.57 | 1.25 | 10.43 | 2.06 |

Effect of the New Compounds on Learning and Memory in a Cognition Impairment Animal Model The new compounds were evaluated for their efficacy as cognition enhancers in a pharmacological model for cognitive impairment. The effects of the new compounds were evaluated in untreated and MK-801-treated rodents (mice or rats). MK-801 is a non-competitive antagonist of the N-Methyl-D-aspartate (NMDA) receptor which impairs animal performance in various learning and memory paradigms (Castellano C et al., *Curr. Drug Targets* 2001; 2:273-83; Riedel G et al., *Behav. Brain Res.* 2003; 140:1-47). MK-801 also produces various effects on rodent behavior, including deficits in sensory processing, hypermotility, stereotypy and ataxia. The behavioral phenotype induced by MK-801 treatment has been widely used as animal model of cognitive deficits (Bardgett M E et al., *Brain Res. Bull.* 2003; 60:131-42; Van der Staay F J et al., *Behav. Brain Res.* 2011; 220:215-29; Mutlu O et al., *Pharmacol. Biochem. Behav.* 2011; 99:557-65).

In order to determine whether the tested compounds act as cognitive enhancer, their ability to restore normal cognitive behavior was tested through widely used tests such as the novel object recognition test (Dere E et al., *Neuroses. Biobehav. Rev.* 2007; 31:673-704; Boess F G et al., *J. Pharmacol. Exp. Ther.* 2007; 321:716-25); the passive or inhibitory avoidance task (Sarter M et al., *Psychopharmacology (Berl)* 1992; 107:144-59); the Morris water maze (D'Hooge R et al., *Brain Res. Rev.* 2001; 36:60-90); and the T-maze alternation task (Boess F G et al., *Neuropharmacology* 2004; 47:1081-92; Spowart-Manning L et al., *Behav. Brain Res.* 2004; 151:37-46).

As a representative example for the evaluation of the new POP inhibitors, the protocol followed for each of the behavioral tests, as well as the results obtained in the object recognition test and the passive avoidance test are described.

Novel Object Recognition Task

The novel object recognition (NOR) task is based on the natural preference of rodents to explore novel objects (Ennaceur A et al., *Behav. Brain Res.* 1988; 31:47-59). It is a relevant non-rewarded test for studying visual learning and memory deficits. Briefly, the NOR task procedure consisted of three trials: habituation, training and retention. Each animal was habituated to a 40-cm diameter circular arena for 10 min in the absence of objects (habituation session). The following day, the animal was placed for 10 min in the circular arena for the training trial, and two identical objects were placed in a symmetrical position. This step was done for two consecutive days. On the third day, one of the objects was replaced by a different object. The object not used in the training trial was used as the novel object in the retention trial. The animals were then allowed to explore freely for 10 min, and the time spent exploring each object was recorded. The animal is expected to spend more time exploring the novel object, which is a sign of intact recognition memory. An index of discrimination was calculated as follows: time spent exploring the new object minus time spent exploring the old object, divided by the total time exploring both objects, and multiplied by 100. A higher index of discrimination was considered to reflect greater memory retention.

The corresponding tested POP inhibitor, freshly dissolved in 5% Tween 80 in PBS, was given subcutaneously (s.c.) at a dose of 5 mg/Kg, in a volume of 0.1 ml per 10 g of animal body weight. Fifteen minutes later, MK-801 dissolved in PBS buffer was injected intraperitoneally (i.p.) at a dose of 0.2 mg/kg, in a volume of 0.1 mL per 10 g of animal body weight. A control group was administered i.p. with MK-801 and s.c. with the same volume of vehicle (PBS with a 5% of Tween 80). Another control group received PBS i.p. and the same volume of vehicle s.c. Drug doses were selected according to behavioral and neurochemical studies, showing that the drugs have the intended effect.

Animals were injected with the two drugs every day during the training period as well as prior to the test session.

The results obtained when administering the compound of Example 4, as a representative of the compounds of the invention, are shown in FIG. 1.

As illustrated with the compound of Example 4, the compounds of the invention are able to reverse MK-801-induced memory impairment in the NOR test.

Passive Avoidance Task

For the evaluation of the passive avoidance task, a two-compartment box with a light compartment and a dark compartment of the same dimensions was used. The two compartments were separated by a guillotine door that could be raised. The apparatus used was according to standard procedures for this test. One shock session and an evaluation session were given, separated by intersession intervals of 24 h. In the shock session, the rodent was placed in the light compartment. After an accommodation period of 20 s, the guillotine door to the other compartment was opened and lowered once again, once the rodent had entered the dark compartment. Then, a short and weak foot shock was administered. The rodent was removed from the apparatus 60 s after shock termination and put back into its home cage. In the evaluation session, the time which the animal takes to enter the dark compartment (in seconds) was measured, as a sign of memory retention of the shock received in the dark compartment during the previous session. A second evaluation session was performed one week after the initial shock session. The corresponding evaluated compound was injected s.c. 35 min before the shock session, followed 15 minutes later by i.p. injection of MK-801, or PBS in the case of the control, in the same doses and volume as described for the object recognition test. The animals treated with MK-801 alone showed little retention of the memory of the shock session, while the animals which had additionally received a POP inhibitor showed a larger latency to enter the dark compartment, indicative of better memory retention.

Figure 2:
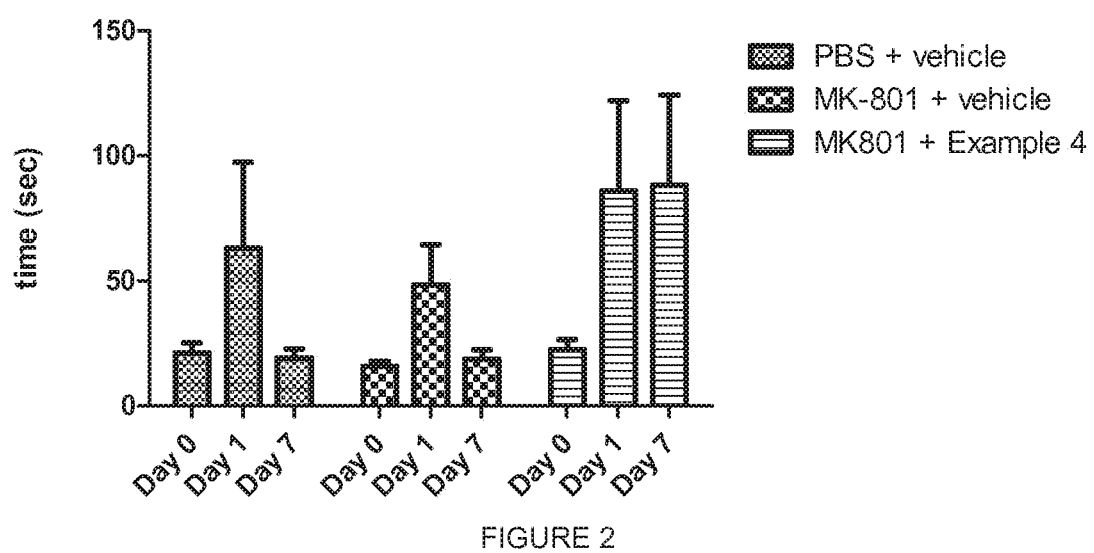
FIG. 2 is graphic comparing the results obtained in the passive avoidance task test for PBS+vehicle, MK-801+vehicle and MK-801 and the compound of example 4.

The results obtained when administering the compound of Example 4, as a representative of the compounds of the invention, are shown in FIG. 2.

As illustrated with the compound of Example 4, the compounds of the invention are able to reverse MK-801-induced memory Impairment in the Passive avoidance test.

Water Maze (Morris Escape Test)

Morris water escape performance was assessed in a water tank, according to standard procedures and dimensions for this test, filled with tap water stained with latex at a temperature of approximately 22° C. The escape platform consisted of a gray polyethylene cylinder, submerged 1.5 cm below the surface of the water. The corresponding evaluated POP inhibitor was administered s.c. 35 min before training and test sessions, followed after 15 min by i.p. injection of MK-801, or PBS in the case of the control, in the same dose and volume as described for the object recognition test. Animals were injected with the two compounds every day during the training sessions, as well as on evaluation sessions.

The rodents received two sets of training sessions during three consecutive days, with an interval of two-days between the two sets. Each training session consisted of two sets of three trials, which were run in close succession. A trial was started by placing the rodent into the pool, facing the wall of the tank. Four starting positions (north, east, south, and west) were used in randomized order. The escape platform was always in the same quadrant. A trial was terminated as soon as the animal had climbed onto the escape platform or when 60 s had elapsed, whichever event occurred first. Once rodents reached the platform, they were allowed to stay for 30 s in order to allow them to associate the scape platform with a specific position on the tank. Then it was taken from the platform and the next trial was started, if an animal did not find the platform within 60 s, it was put on the platform by the experimenter and was allowed to stay there for 30 s. During the first training session a visual clue was placed to mark the position of the platform. This clue was removed for the following sessions. During the training sessions the latency to reach the platform was recorded.

The day after the second set of training sessions was finished, an evaluation was performed: the platform was removed, and the time the rodent spent in the quadrant of the pool where the platform had been positioned during the training sessions (target quadrant) was measured during 60 s. In the probe trial, all animals were released from the same start position, opposite to the target quadrant. Animals treated with MK-801 were not able to effectively learn and remember where the platform stood, as shown by longer swum distances and escape latency, as well as the time these animals spent on the target quadrant, which was about average compared to the other quadrants. Animals which were treated with MK-801 and with the corresponding POP inhibitor showed a better performance on the test, learning the position of the platform (as reflected on higher percentage of time spent in the target quadrant), thus showing that the effect of MK-801 was effectively reversed. The animals were left to rest for a week and trained afterwards for 4 additional days. On the fifth day the platform was removed and a second evaluation was performed.

T-Maze Alternation Task

Working memory was tested using a T-maze alternation task. The experiments were performed in a T-maze constructed of wood and painted black, according to general dimensions and procedure. The side alleys were closed off from the main alley by movable doors. A week before habituation, all animals were partially food restricted and remained that way throughout the remaining part of the experiment, in order to keep the animals at 85% of their free-feeding body weight. A video camera was situated ~1 m above the T-maze to videotape the test session. The T-maze was cleaned between different animals but not between different trials. The full experiment consisted of three parts: habituation, training, and testing. During habituation, all animals were placed on the T-maze until they ate two pieces of food or 90 s had elapsed. This was repeated three times a day for 5 d. During training, all animals received six trials a day per day. Each trial consisted of two runs: a forced run and a free run. On the forced run, rodents were forced to obtain a piece of food from one goal arm of the T-maze, with the other goal arm blocked by its door. Animals were then placed back into the start arm for 10 s delay period. At the beginning of the free run, the animals were allowed to choose either goal arm. If the animals chose the arm opposite to the one they had been forced into during the forced run, they received the food reward. If the animals chose the same arm into which they had been forced, they received no food reward. There was a 5 min inter-trial interval. The training period ended after control animals made >70% correct choices on 2 consecutive days. Animals took 7-12 days to reach the criterion. Animals that did not reach the criterion by 14 days were rejected from the study. Rodents were then tested for their performance at 10 or 40 s delay periods. Animals were given three 10 s delay and three 40 s delay trials during the day of testing. For drug testing, rodents were given six 10 s delay trials 15 min after drug exposure. The sequence of delays and forced-run food locations (either left or right) were randomized each day, as long as the same delay or the same forced-arm location was not used for three trials in a row. Goal entries were defined as placing four paws in the arm.

The corresponding evaluated POP inhibitor was injected s.c. 35 min before the test session, followed 15 minutes later by i.p. injection of MK-801, or PBS in the case of the control, in the same doses and volume as described for the object recognition test.

Control animals showed learning curves with near-chance level performance (around 50% of correct arm entries) between days 1 and 4 of training, and a gradual improvement between days 11 and 14 of the training until reaching a plateau of 70% correct arm entries. Their performance remained stable at 10 and 40 s delay trials. Animals treated with MK-801 were not able to effectively learn the alternation task and performed below chance level in the delay trials. Animals which were treated with MK-801 and with the corresponding POP inhibitor showed a better performance on the test, with similar learning curves as the control animals and retaining memory in the delay trials, thus showing that the effect of MK-801 was effectively reversed.

The invention claimed is:

1. A method for the treatment of a cognitive disorder in a patient, comprising administering to the patient in need of such treatment a therapeutic amount of a compound of formula (I):

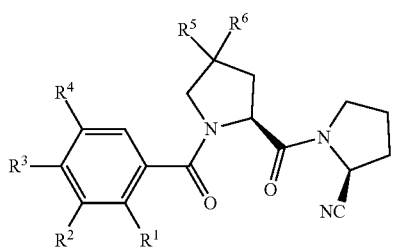

(I)

wherein
$R^1$, $R^2$, $R^3$ and $R^4$ are independently selected from the group consisting of $C_{1-4}$ alkoxy, $C_{1-4}$ alkylcarbonyloxy, benzyloxy, phenylcarbonyloxy, naphthylcarbonyloxy, quinolinylcarbonyloxy, isoquinolinylcarbonyloxy, trifluoromethyl, halogen and hydrogen;
$R^5$ is selected from the group consisting of halogen, nitrile, $C_{1-4}$ alkoxy, $C_{1-4}$ alkylthio, $C_{1-4}$ alkyl, phenyl, phenoxy, phenylthio and trifluoromethyl;
$R^6$ is selected from the group consisting of hydrogen, fluoro and methyl;
or a pharmaceutically acceptable salt, isomer, prodrug or solvate thereof.

2. The method according to claim 1, wherein the cognitive disorder is a cognitive disorder associated with a disease selected from the group consisting of schizophrenia, bipolar affective disorder, Alzheimer's disease and Parkinson's disease.

3. The method according to claim 1, wherein $R^2$ and $R^4$ are independently selected from the group consisting of hydrogen, halogen, trifluoromethyl and $C_{1-4}$ alkoxy.

4. The method according to claim 3, wherein $R^2$ is selected from the group consisting of hydrogen and methoxy and $R^4$ is selected from the group consisting of fluoro, trifluoromethyl and methoxy.

5. The method according to claim 1, wherein $R^3$ is a benzyloxy.

6. The method according to claim 1, wherein $R^5$ is fluoro.

7. The method according to claim 1, wherein $R^6$ is hydrogen or fluoro.

8. The method according to claim 1, wherein said compound is selected from the group consisting of:
(S)-1-((2S,4R)-1-(4-(benzyloxy)-3,5-dimethoxybenzoyl)-4-methoxypyrrolidine-2-carbonyl)pyrrolidine-2-carbonitrile;
(S)-1-((2S,4R)-1-(4-(benzyloxy)-3,5-dimethoxybenzoyl)-4-fluoropyrrolidine-2-carbonyl)pyrrolidine-2-carbonitrile;
(S)-1-((2S,4S)-1-(4-(benzyloxy)-3,5-dimethoxybenzoyl)-4-phenylpyrrolidine-2-carbonyl)pyrrolidine-2-carbonitrile;
(S)-1-((2S)-1-(4-(benzyloxy)-3,5-dimethoxybenzoyl)-4,4-difluoropyrrolidine-2-carbonyl)pyrrolidine-2-carbonitrile;
(S)-1-((2S,4S)-1-(4-(benzyloxy)-3,5-dimethoxybenzoyl)-4-(methylthio)pyrrolidine-2-carbonyl)pyrrolidine-2-carbonitrile;
(S)-1-((2S,4S)-1-(4-(benzyloxy)-3,5-dimethoxybenzoyl)-4-methylpyrrolidine-2-carbonyl)pyrrolidine-2-carbonitrile;
(S)-1-((2S,4R)-1-(4-(benzyloxy)-3,5-dimethoxybenzoyl)-4-cyanopyrrolidine-2-carbonyl)pyrrolidine-2-carbonitrile;
(S)-1-((2S,4S)-1-(4-(benzyloxy)-3,5-dimethoxybenzoyl)-4-(trifluoromethyl)-pyrrolidine-2-carbonyl)pyrrolidine-2-carbonitrile;
(S)-1-((2S,4R)-1-(4-(benzyloxy)-3,5-dimethoxybenzoyl)-4-(tert-butoxy)pyrrolidine-2-carbonyl)pyrrolidine-2-carbonitrile;
(S)-1-((2S,4R)-1-(4-(benzyloxy)-3,5-dimethoxybenzoyl)-4-acetoxypyrrolidine-2-carbonyl)pyrrolidine-2-carbonitrile;
(S)-1-((2S)-1-(4-acetoxy-3,5-dimethoxybenzoyl)-4,4-difluoropyrrolidine-2-carbonyl)pyrrolidine-2-carbonitrile;
(S)-1-((2S)-1-(4-benzoyloxy-3,5-dimethoxybenzoyl)-4,4-difluoropyrrolidine-2-carbonyl)pyrrolidine-2-carbonitrile;
(S)-1-((2S)-1-(3,4-dibenzyloxy-5-methoxybenzoyl)-4,4-difluoropyrrolidine-2-carbonyl)pyrrolidine-2-carbonitrile;
(S)-1-((2S)-1-(3,4-dibenzoyloxy-5-methoxybenzoyl)-4,4-difluoropyrrolidine-2-carbonyl)pyrrolidine-2-carbonitrile;
(S)-1-((2S)-1-(3-acetoxy-4,5-dimethoxybenzoyl)-4,4-difluoropyrrolidine-2-carbonyl)pyrrolidine-2-carbonitrile; and
(S)-1-((2S)-1-(3-pivaloyloxy-4,5-dimethoxybenzoyl)-4,4-difluoropyrrolidine-2-carbonyl)pyrrolidine-2-carbonitrile;
or a pharmaceutically acceptable salt, isomer, prodrug or solvate thereof.

9. The method according to claim 1, wherein said compound is selected from the group consisting of:
(S)-1-((S)-1-(4-(benzyloxy)benzoyl)-4,4-difluoropyrrolidine-2-carbonyl)pyrrolidine-carbonitrile;
(S)-1-((S)-1-(3-(benzyloxy)benzoyl)-4,4-difluoropyrrolidine-2-carbonyl)pyrrolidine-2-carbonitrile;
(S)-1-((S)-1-(2-(benzyloxy)benzoyl)-4,4-difluoropyrrolidine-2-carbonyl)pyrrolidine-2-carbonitrile;
(S)-1-((S)-1-(4-(benzyloxy)-3-(trifluoromethyl)benzoyl)-4,4-difluoropyrrolidine-2-carbonyl)pyrrolidine-2-carbonitrile; and
(S)-1-((S)-1-(4-(benzyloxy)-3-fluorobenzoyl)-4,4-difluoropyrrolidine-2-carbonyl)pyrrolidine-2-carbonitrile;
or a pharmaceutically acceptable salt, isomer, prodrug or solvate thereof.

10. The method according to claim 4, wherein $R^2$ and $R^4$ are methoxy.

11. The method according to claim 1, wherein $R^2$ and $R^4$ are independently selected from the group consisting of $C_{1-4}$ alkoxy, $C_{1-4}$ alkylcarbonyloxy, and benzyloxy.

12. The method according to claim 1, wherein $R^1$ is hydrogen.

13. The method according to claim 1, wherein $R^5$ is selected from the group consisting of fluoro, methoxy, methylthio, and phenyl.

14. The method according to claim 1, wherein
$R^1$ is hydrogen;
$R^2$, $R^3$ and $R^4$ are independently selected from the group consisting of $C_{1-4}$ alkoxy, $C_{1-4}$ alkylcarbonyloxy, benzyloxy, phenylcarbonyloxy, naphthylcarbonyloxy, and quinolinylcarbonyloxy; and
$R^5$ and $R^6$ are as defined in claim 1;
or a pharmaceutically acceptable salt, isomer, prodrug or solvate thereof.

15. The method according to claim 1, wherein the compound of formula (I), or a pharmaceutically acceptable salt, isomer, prodrug, or solvate thereof, is administered to the patient in a pharmaceutical composition.

16. The method according to claim 15, wherein the pharmaceutical composition is an oral pharmaceutical composition.

17. The method according to claim 16, wherein the oral pharmaceutical composition is selected from the group consisting of a tablet, a pill, a caplet, a gel, a cap, a chewing gum, a capsule, a granule, a drop, a syrup, and a solution.

18. The method according to claim 15, wherein the pharmaceutical composition is formulated for non-parenteral intranasal administration.

19. The method according to claim 18, wherein the pharmaceutical composition is a liquid solution or suspension.

* * * * *